(12) United States Patent
Neitz et al.

(10) Patent No.: US 10,787,707 B2
(45) Date of Patent: Sep. 29, 2020

(54) METHODS AND REAGENTS FOR PREDICTING PREDISPOSITION TO REFRACTIVE ERROR

(71) Applicant: UNIVERSITY OF WASHINGTON, Seattle, WA (US)

(72) Inventors: Jay Neitz, Seattle, WA (US); Maureen Neitz, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/553,418

(22) PCT Filed: Feb. 29, 2016

(86) PCT No.: PCT/US2016/020033
§ 371 (c)(1),
(2) Date: Aug. 24, 2017

(87) PCT Pub. No.: WO2016/138512
PCT Pub. Date: Sep. 1, 2016

(65) Prior Publication Data
US 2018/0112268 A1   Apr. 26, 2018

Related U.S. Application Data

(60) Provisional application No. 62/126,284, filed on Feb. 27, 2015.

(51) Int. Cl.
*C12Q 1/6883* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,800,992 A | 9/1998 | Fodor et al. |
| 6,582,908 B2 | 6/2003 | Fodor et al. |
| 6,706,867 B1 | 3/2004 | Lorenz |
| 6,800,992 B2 | 10/2004 | Wada et al. |
| 8,951,729 B2 | 2/2015 | Neitz et al. |
| 2003/0082576 A1 | 5/2003 | Jones et al. |
| 2004/0110179 A1 | 6/2004 | Shuber et al. |
| 2005/0208555 A1 | 9/2005 | Ralmond et al. |
| 2010/0021889 A1 | 1/2010 | Juo |
| 2012/0014977 A1 | 1/2012 | Furihata et al. |
| 2012/0182520 A1 | 7/2012 | Neitz et al. |
| 2013/0203064 A1 | 8/2013 | Furihata et al. |
| 2014/0080900 A1 | 3/2014 | Neitz et al. |

FOREIGN PATENT DOCUMENTS

| | | |
|---|---|---|
| CN | 103314116 | 4/2018 |
| JP | 2014-504873 | 2/2014 |
| WO | WO2010075319 | 7/2010 |
| WO | WO2011034947 | 3/2011 |
| WO | WO 2012/097213 A2 | 7/2012 |

OTHER PUBLICATIONS

The International Search Report (ISR) with Written Opinion for PCT/US2016/020033 dated Jun. 3, 2016, pp. 1-12.
Gardner, Jessica C. et al, "Three Different Cone Opsin Gene Array Mutational Mechanisms with Genotype-Phenotype Correlation and Functional Investigation of Cone Opsin Variants" Human Mutation (2014) vol. 35(11), pp. 1354-1362.
Ueyama, Hisao et al. "Unique haplotype in exon 3 of cone opsin mRNA affects splicing of its precursor, leading to congenital color vision defect" Biochemical and Biophysical Research Communications (2012) vol. 424, pp. 152-157.
McClements, Michelle et al. "Variations in Opsin Coding Sequences Cause X-Linked Cone Dysfunction Syndrome with Myopia and Dichromacy" Investigative Ophthalmology & Visual Science (2013) vol. 54(2), pp. 1361-1369.
Ars, et al., "Mutations affecting mRNA splicing are the most common molecular defects in patients with neurofibromatosis type 1," Human Molecular Genetics, vol. 9, No. 2, pp. 237-247, 2000.
Blencowe, "Exonic splicing enhancers: mechanism of action, diversity and role in human genetic diseases," TIBS, vol. 25, pp. 106-110, 2000.
Carroll, et al., "Deletion of the X-linked opsin gene array locus control region (LCR) results in disruption of the cone mosaic," Vision Research, vol. 50, pp. 1989-1999, 2010.
Carroll, et al., "Functional photoreceptor loss revealed with adaptive optics: An alternate cause of color blindness," PNAS, vol. 101, No. 22, pp. 8461-8466, 2004.
Carroll, et al., "The Effect of Cone Opsin Mutations on Retinal Structure and the Integrity of the Photoreceptor Mosaic," IOVS, vol. 53, No. 13, pp. 8006-8015, 2012.
Cartegni, et all., "ESEfinder: a web resource to identify exonic splicing enhancers," Nucleic Acids Research, 2003, vol. 31, No. 13, pp. 2003.
Cooper, et al., "RNA and Disease," Cell, vol. 136, pp. 777-793, 2009.
Crognale, et al., "Characterization of a novel form of X-linked incomplete achromatopsia," Visual Neuroscience, vol. 21, pp. 197-203, 2004.
Desmet, et al., "Human Splicing Finder: an online bioinformatics tool to predict splicing signals," Nucleic Acids Research, vol. 37, No. 9, 14 Pages, 2009.

(Continued)

*Primary Examiner* — Carla J Myers
(74) *Attorney, Agent, or Firm* — McDonnell Boehnen Hulbert & Berghoff LLP

(57) ABSTRACT

Methods and reagents for determining a subject's predisposition for refractive error based on the presence of opsin gene exon 3 splicing defects are provided. In one aspect, the invention provides methods for determining a subject's predisposition for refractive error comprising: (a) testing a biological sample obtained from the subject to determine exon 3 splicing defects in one or more opsin gene; and (b) correlating the exon 3 splicing defects in the one or more opsin gene with a predisposition for refractive error.

13 Claims, 8 Drawing Sheets
Specification includes a Sequence Listing.

(56) References Cited

OTHER PUBLICATIONS

Fairbrother, et al., "Predictive Identification of Exonic Splicing Enhancers in Human Genes," Science, vol. 297, No. 5583, vol. 1007-1013, 2002.

Gardner, et al., "Three Different Cone Opsin Gene Array Mutational Mechanisms with Genotype-Phenotype Correlation and Functional Investigation of Cone Opsin Variants," Human Mutation, vol. 35, No. 11, pp. 1354-1362, 2014.

Greenwald, et al., "S-opsin knockout mice with the endogenous M-opsin gene replaced by an L-opsin variant," Visual Neuroscience, vol. 32, pp. 25-37, 2014.

Kuchenbecker, et al., "Cone-isolating On-Off electroretinogram for studying chromatic pathways in the retina," J Opt Soc Am A Opt Image Sci Vis, vol. 31, No. 4, pp. A208-A213, 2014.

McClements, et al., "Variations in Opsin Coding Sequences Cause X-Linked Cone Dysfunction Syndrome with Myopia and Dichromacy," IOVS, vol. 54, No. 2, pp. 1361-1369, 2013.

McClements, et al., "Bornholm Eye Disease Arises From a Specific Combination of Amino Acid Changes Encoded by Exon 3 of the L/M Cone Opsin Gene," Investigative Ophthalmology & Visual Science, vol. 51, 2609, 2 pages, 2010.

Mizrahi-Meissonnier, et al., "Variable Retinal Phenotypes Caused by Mutations in the X-Linked Photopigment Gene Array," Biochemistry and Molecular Biology, vol. 51, No. 8, pp. 3884-3892, 2010.

Neitz, et al., "Spectral Tuning of Pigments Underlying Red-Green Color Vision," Science, vol. 252, No. 5008, pp. 971-974, 1991.

Neitz, et al., "The genetics of normal and defective color vision," Vision Research, vol. 51, pp. 633-651, 2011.

Neitz, et al., "Variety of genotypes in males diagnosed as dichromatic on a conventional clinical anomaloscope," Visual Neuroscience, vol. 21, pp. 205-216, 2004.

Oh, et al., "Comparison of the Clinical Expression of Retinitis Pigmentosa Associated With Rhodopsin Mutations at Codon 347 and Codon 23," American Journal of Ophthalmology, vol. 136, No. 2, pp. 306-313, 2003.

Pagani, et al., "Genomic variants in exons and introns: identifying the splicing spoilers," Nature Reviews Genetics, vol. 5, pp. 389-396, 2004.

Pagani, et al., "New type of disease causing mutations: the example of the composite exonic regulatory elements of splicing in CFTR exon 12," Human Molecular Genetics, vol. 12, No. 10, pp. 1111-1120, 2003.

Sironi, et al., "Silencer elements as possible inhibitors of pseudoexon splicing," Nucleic Acids Research, vol. 32, No. 5, pp. 1783-1791, 2004.

Teraoka, et al., "Splicing Defects in the Ataxia-Telangiectasia Gene, ATM: Underlying Mutations and Consequences," Am. J. Hum. Genet., vol. 64, pp. 1617-1631, 1999.

Ueyama, et al., "Unique haplotype in exon 3 of cone opsin mRNA affects splicing of its precursor, leading to congenital color vision defect," Biochemical and Biophysical Research Communications, vol. 424, pp. 152-157, 2012.

Wang, et al., "Systematic Identification and Analysis of Exonic Splicing Silencers," Cell, vol. 119, pp. 831-845, 2004.

Ward, et al., "The pathobiology of splicing," Journal of Pathology, vol. 220, pp. 152-163, 2010.

Weleber, et al., "Retinitis Pigmentosa and Allied Disorders," Ophthalmology, vol. 2, p. 761, 2012.

Zhang, et al., "Computational definition of sequence motifs governing constitutive exon splicing," Genes & Development, pp. 1241-1250, 2004.

Zhang, et al., "RNA landscape of evolution for optimal exon and intron discrimination," PNAS, vol. 105, No. 15, pp. 5797-5802, 2008.

Ahern, H. "Biochemical, Reagents Kits Offer Scientists Good Return on Investment" The Scientist. Jul. 1995. 9(15): 20-25.

Applied Biosystems. Product Bulletin. Automated DNA Sequencing. ABI PRISM® BigDyeTM Primer Sequencing Kit. 2000. available via url: <tools.thermofisher.com/content/sfs/brochures/cms_040730.pdf> ).

Carkeet, et al. Optometry and Vision Science 81, 829, 2004.

Carroll et al., Proceedings of the National Academy of Sciences of the United States of America 106, 20948, 2009.

Carroll, et al., Journal of the Optical Society of America A 17,499, 2000.

Carroll, et al., Journal of Vision 2, 531, 2002.

Drummond-Borg, et al., Proceedings of the National Academy of Sciences of the United States of America 86983, 1989.

GenCard for the OPN1LW gene available via url: <genecards.org/cgi-bin/carddisp.pl?geneOPN1LW>, printed on Feb. 19, 2014. 20 pages.

GeneCard for the OPN1MW gene available via url: <genecards.org/cgi-bin/carddisp.pl?geneOPN1MW>, printed on Feb. 19, 2014. 1 page.

Gunther and Dobkins Vision Research 42:1367-1378, 2002.

Gwiazda et al., Investigative Ophthalmology & Visual Science 44, 1492, 2003.

Hahner et al., International Congress Series (2003), vol. 1239, pp. 11-16.

Halushka et al., Nature (Jul. 1999) vol. 22, pp. 239-247.

Hattersley et al., The Lancet. (2005) vol. 366, pp. 1315-1323.

Hirschhorn et al., Genetics in Medicine (2002) vol. 4(2), pp. 45-61.

Hofer, et al., Journal of Neuroscience 25, 9669, 2005.

Kuchenbecker et al, Vis. Neurosci. 25(3):301-6, 2008.

Lucentini et al., The Scientist (2004) vol. 18, p. 20.

McClements et al., Invest Ophthalmol Vis Sci., 51(9):4771-4780 (Sep. 2010).

McMahon, et al., Journal of Vision, 8, 1, 2008.

Michaelides et al., Ophthalmology 112, 1448, 2005.

Michaelides, et al. (2010) "The PROM1 mutation p.R373C causes an autosomal dominant bull's eye maculopathy associated with rod, rod-cone, and macular dystrophy," IOVS, 51(9): 4771-4780.

Mizrahi-Meissonnier et al, Investigative Ophthalmology and Visual Science, pp. 1-30, (Mar. 2010).

Nathans et al., Science 245, 831, 1989.

Nathans, et al. Science 232, 203, 1986.

National Center for Biotechnology Information, National Library of Medicine (Bethesda, MD, USA), NCBI SNP Database printout for the OPN1 LW gene, printed on Feb. 20, 2014. Six pages.

National Center for Biotechnology Information, National Library of Medicine (Bethesda, MD, USA), NCBI SNP Database printout for the OPN1MW Gene, printed on Feb. 20, 2014. Two pages.

NCBI Database GenBank Accession No. NM 000513.01 (OPN1MW); Nov. 2009. National Center for Biotechnology Information, National Library of Medicine, Bethesda, MD, USA); printed Mar. 16, 2017, four pages.

NCBI Database GenBank Accession No. NM 020061.01 (OPN1LW); Nov. 2009. National Center for Biotechnology Information, National Library of Medicine, Bethesda, MD, USA); printed Mar. 17, 2019, four pages.

Neitz and Neitz, J_ Vis. 2:531-42, 2002.

Neitz et al., IOVS. ARVO (2011) Abstracts, Program 4896, Poster #A229. One page.

Neitz et al., Vision Research 35: 2395-2407, 1995.

Neitz, et al., Color Research & Application 26, S239, 2001.

Oda et al. (2003) "Analysis of L-cone/M-cone visual pigment gene arrays in females by long-range PCR" Vision Research, vol. 43, pp. 489-495.

Radhakrishna et al., "The X-linked severe form of myopia locus at Xq28 (MYP1): Narrowing of the critical region and exclusion of twelve known genes localized in the interval." Investigative Ophthalmology & Visual Science supplement (abstract #3814), 2005, one page.

Scholl et al., (2006) "Progressive cone dystrophy with deutan genotype and phenotype", Graefe's ArchIin Exp Ophthalmol, vol. 244, pp. 183-191.

Scholl et al., "Macular dystrophy with protan genotype and phenotype studied with cone type specific ERGs" Current Eye Research, vol. 22(3):221-228 (2001).

(56) References Cited

OTHER PUBLICATIONS

Schwartz, M. Haim, D. Skarsholm, Clinical Genetics 38, 281, 1990.
Twelker et al., Optometry and Vision Science 86,918, 2009.
Verrelli, et al., American Journal of Human Genetics 75, 363, 2004.
Winderickx et al., Nature Genetics 1, 251, 1992.
Winderickx, et al. (1993) "Haplotype diversity in the human red and green opsin genes: evidence for frequent sequence exchange in exon 3," Human Molecular Genetics, 2(9):1413-1421.
Young et al., "X-Linked High Myopia Associated with Cone Dysfunction" Archives of Ophthalmology 122:897-908 (Jun. 2004).
Young, et al., (2001) "Further refinement of the MYP2 locus for autosomal dominant high myopia by linkage disequilibrium analysis", Ophthalmic Genetics, vol. 22, pp. 69-75.
Mummidi et al., "Evolution of Human and Non-human Primate CC Chemokine Receptor 5 Gene and mRNA" Journal of Biological Chemistry, 275(25):18946-61 (Jun. 2000).
Hysi et al., "A genome-wide association study for myopia and refractive error identifies a susceptibility locus at 15q25," Nat Genet, 42(10):902-05 (Oct. 2010).

SEQUENCE LISTING

<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Leu Ile Val Val Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Leu Ile Ala Val Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Leu Ile Ala Val Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Leu Val Ala Val Ala
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Leu Ile Ala Ile Ser
1               5

<210> SEQ ID NO 6
<211> LENGTH: 463
<212> TYPE: DNA
<213> ORGANISM: Artificial Sequence
<220> FEATURE:
<223> OTHER INFORMATION: Synthetic

<400> SEQUENCE: 6

```
gccccttcga aggcccgaat taccacatcg ctcccagatg ggtgtaccac ctcaccagtg      60
tctggatgat ctttgtggtc aytgcatccg tcttcacaaa tgggcttgtg ctggcggcca    120
ccatgaagtt caagaagctg cgccacccgc tgaactggat cctggtgaac ctggcggtcg    180
ctgacctrgc agagaccgtc atcgccagca ctatcagcrt tgtgaaccag gtmtctggct    240
acttcgtgct gggccaccct atgtgtgtcc tggagggcta caccgtctcc ctgtgtggta    300
ctggccccac ggcctgaaga cttcatgcgg cccagacgtg ttcagcggca gctcgtaccc    360
cggggtgcag tcttacatga ttgtcctcat ggtcacctgc tgcatcaycc cactcrysat    420
catcrtgctc tgctacctcc aagtgtggct ggccatccga gcg                      463
```

<210> SEQ ID NO 7
<211> LENGTH: 65
<212> TYPE: DNA
<213> ORGANISM: Artificial Sequence
<220> FEATURE:
<223> OTHER INFORMATION: Synthetic

<400> SEQUENCE: 7

```
tctggctact cgtgctgggc ccaccctatg tgtgtcctgg agggctacac cgtctccctg     60
tgtgg                                                                 65
```

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Met Ile Ala Val Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Leu Val Val Val Ala
1               5

<210> SEQ ID NO 10
<211> LENGTH: 111
<212> TYPE: DNA
<213> ORGANISM: Artificial Sequence
<220> FEATURE:
<223> OTHER INFORMATION: Synthetic

<400> SEQUENCE: 10

```
ggtactggcc ccacggcctg aagacttcat gcggcccaga cgtgttcagc ggcagctcgt     60
accccggggt gcagtcttac atgattgtcc tcatggtcac ctgctgcatc a             111
```

<210> SEQ ID NO 11
<211> LENGTH: 112
<212> TYPE: DNA
<213> ORGANISM: Artificial Sequence
<220> FEATURE:
<223> OTHER INFORMATION: Synthetic

```
<400> SEQUENCE: 11
atggcccagc agtggagcct ccaaaggctc gcaggccgcc atccgcagga cagctatgag    60
gacagcaccc agtccagcat cttcacctac accaacagca actccaccag ag          112

<210> SEQ ID NO 12
<211> LENGTH: 111
<212> TYPE: DNA
<213> ORGANISM: Artificial Sequence
<220> FEATURE:
<223> OTHER INFORMATION: Synthetic

<400> SEQUENCE: 12
tttcgaaact gcatcttgca gcttttcggg aagaaggttg acgatggctc tgaactctcc    60
agcgcctcca aaacggaggt ctcatctgtg tcctcggtat cgcctgcatg a            111

<210> SEQ ID NO 13
<211> LENGTH: 169
<212> TYPE: DNA
<213> ORGANISM: Artificial Sequence
<220> FEATURE:
<223> OTHER INFORMATION: Synthetic

<400> SEQUENCE: 13
ggatcacagg tctctggtct ctggccatca tttcctggga gagrtggmtg gtggtstgca    60
agcccttggg caatgtgaga tttgatgcca agctggccat crtkggcatt gycttctcct   120
ggrtctggkc tgctgtgtgg acagccccgc ccatctttgg ttggagcag              169

<210> SEQ ID NO 14
<211> LENGTH: 297
<212> TYPE: DNA
<213> ORGANISM: Artificial Sequence
<220> FEATURE:
<223> OTHER INFORMATION: Synthetic

<400> SEQUENCE: 14
gccccttcga aggcccgaat taccacatcg ctcccagatg ggtgtaccac ctcaccagtg    60
tctggatgat ctttgtggtc aytgcatccg tcttcacaaa tgggcttgtg ctggcggcca   120
ccatgaagtt caagaagctg cgccacccgc tgaactggat cctggtgaac ctggcggtcg   180
ctgacctrgc agagaccgtc atcgccagca ctatcagcrt tgtgaaccag gtmtctggct   240
acttcgtgct gggccaccct atgtgtgtcc tggagggcta caccgtctcc ctgtgtg      297

<210> SEQ ID NO 15
<211> LENGTH: 166
<212> TYPE: DNA
<213> ORGANISM: Artificial Sequence
<220> FEATURE:
<223> OTHER INFORMATION: Synthetic

<400> SEQUENCE: 15
gtactggccc cacggcctga agacttcatg cggcccagac gtgttcagcg gcagctcgta    60
ccccggggtg cagtcttaca tgattgtcct catggtcacc tgctgcatca yccactcry   120 satcatcrtg ctctgctacc tccaagtgtg gctggccatc cgagcg                 166

<210> SEQ ID NO 16
<211> LENGTH: 167
<212> TYPE: DNA
<213> ORGANISM: Artificial Sequence
<220> FEATURE:
<223> OTHER INFORMATION: Synthetic
```

<400> SEQUENCE: 16
ggtactggcc ccacggcctg aagacttcat gcggcccaga cgtgttcagc ggcagctcgt    60
accccggggt gcagtcttac atgattgtcc tcatggtcac ctgctgcatc ayccactcr    120 ysatcatcrt gctctgctac ctccaagtgt ggctggccat ccgagcg                 167

<210> SEQ ID NO 17
<211> LENGTH: 169
<212> TYPE: DNA
<213> ORGANISM: Artificial Sequence
<220> FEATURE:
<223> OTHER INFORMATION: Synthetic

<400> SEQUENCE: 17
ggatcacagg tctctggtct ctggccatca tttcctggga gagrtggmtg gtggtstgca    60 agcccttttgg caatgtgaga tttgatgcca agctggccat crtkggcatt gycttctcct   120
ggrtctggkc tgctgtgtgg acagccccgc ccatctttgg ttggagcag                169

<210> SEQ ID NO 18
<211> LENGTH: 30
<212> TYPE: DNA
<213> ORGANISM: Artificial Sequence
<220> FEATURE:
<223> OTHER INFORMATION: Synthetic

<400> SEQUENCE: 18
acgttggatg aaccaggtct ctggctactt                                     30

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
aaccaggtct ctggctactt                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
catgtaagac tgcaccccgg                                                20

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
aggccgtggg gccagtacc                                                 19

<210> SEQ ID NO 22
<211> LENGTH: 20
<212> TYPE: DNA
<213> ORGANISM: Artificial Sequence
<220> FEATURE:
<223> OTHER INFORMATION: Synthetic

```
<400> SEQUENCE: 22
ccggggtgca gtcttacatg                                                      20

<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
ggtactggcc ccacggcct                                                       19

<210> SEQ ID NO 24
<211> LENGTH: 1092
<212> TYPE: DNA
<213> ORGANISM: Artificial Sequence
<220> FEATURE:
<223> OTHER INFORMATION: Synthetic

<400> SEQUENCE: 24
cgtgaccctc aggtgatgcg ccagggccgg ctgccgtcgg ggacagggct ttccatagcc          60
atggcccagc agtggagcct ccaaaggctc gcaggccgcc atccgcagga cagctatgag        120
gacagcaccc agtccagcat cttcacctac accaacagca actccaccag aggcccttc         180 gaaggcccga attaccacat cgctcccaga tgggtgtacc acctcaccag tgtctggatg        240
atctttgtgg tcactgcatc cgtcttcaca aatgggcttg tgctggcggc caccatgaag        300
ttcaagaagc tgcgccaccc gctgaactgg atcctggtga acctggcggt cgctgaccta        360
gcagagaccg tcatcgccag cactatcagc attgtgaacc aggtctctgg ctacttcgtg        420
ctgggccacc ctatgtgtgt cctggagggc tacaccgtct ccctgtgtgg tactggcccc        480
acggcctgaa gacttcatgc ggcccagacg tgttcagcgg cagctcgtac cccggggtgc        540
agtcttacat gattgtcctc atggtcacct gctgcatcat cccactcgct atcatcatgc        600
tctgctacct ccaagtgtgg ctggccatcc gagcggtggc aaagcagcag aaagagtctg        660 aatccacccca gaaggcagag aaggaagtga cgcgcatggt ggtggtgatg atctttgcgt       720
actgcgtctg ctggggaccc tacaccttct tcgcatgctt tgctgctgcc aaccctggtt        780
acgccttcca ccctttgatg gctgccctgc cggcctactt tgccaaaagt gccactatct        840
acaaccccgt tatctatgtc tttatgaacc ggcagtttcg aaactgcatc ttgcagcttt        900
tcgggaagaa ggttgacgat ggctctgaac tctccagcgc ctccaaaacg gaggtctcat        960
ctgtgtcctc ggtatcgcct gcatgaggtc tgcctcctac ccatcccgcc caccggggct       1020
ttggccacct ctcctttccc cctccttctc catccctgta aaataaatgt aatttatctt       1080
tgccaaaacc aa                                                           1092
```

METHODS AND REAGENTS FOR PREDICTING PREDISPOSITION TO REFRACTIVE ERROR

CROSS REFERENCE

This application is a U.S. national phase of International Application No. PCT/US2016/020033, filed on Feb. 29, 2016, which claims priority to U.S. Provisional Application No. 62/126,284 filed Feb. 27, 2015, both of which are incorporated by reference herein in their entirety.

BACKGROUND

Many human diseases involve gene-splicing errors, including cystic fibrosis, Duchenne muscular dystrophy, and retinitis pigmentosa. The L and M cone opsin genes, designated OPN1LW and OPN1MW, respectively, encode the L and M photopigments and each are highly variable in the sequences of exon 2, 3 and 4. Recently, Ueyama et al (Biochem. Biophys. Res. Commun., 424, 152, 2012) found that variants of the cone opsin genes associated with red-green color vision deficiency led to splicing errors that resulted in the absence of exon 3 from the final mRNA. However, the impact of splicing errors in the L and M cone opsin genes on refractive error are unknown.

SUMMARY OF THE INVENTION

In one aspect, the invention provides methods for determining a subject's predisposition for refractive error comprising:

(a) testing a biological sample obtained from the subject to determine exon 3 splicing defects in one or more opsin gene; and (b) correlating the exon 3 splicing defects in the one or more opsin gene with a predisposition for refractive error.

In one embodiment, the testing comprises testing the biological sample obtained from the subject to determine the relative amount of full length opsin gene mRNA compared to exon 3-skipped opsin gene mRNA ("EX3(−) mRNA"); and wherein the correlating comprises correlating the relative amount of full length opsin gene mRNA to EX3(−) mRNA with a predisposition for refractive error. In a further embodiment determining the relative amount of full length opsin gene mRNA to EX3(−) mRNA comprises (i) generating amplification products from cDNA of opsin gene mRNA present in the biological sample, wherein the amplification products span exon 3; and (ii) detecting amplification products corresponding to full length opsin gene mRNA and amplification products corresponding to EX3(−) mRNA. In a further embodiment, detecting the amplification products comprises generating a primer extension product from the amplification products using a primer that binds to the amplification products adjacent to an end of exon 3.

In another embodiment, determining the relative amount of full length opsin gene mRNA to EX3(−) mRNA comprises (i) generating cDNA of opsin gene mRNA present in the biological sample; and (ii) detecting cDNA corresponding to full length opsin gene mRNA and cDNA corresponding to EX3(−) mRNA. In one embodiment, the detecting comprises (i) contacting the cDNA with a primer pair that spans exon 3 and is capable of selectively amplifying the one or more opsin gene, under conditions suitable for amplification of the cDNA, and (ii) amplifying the cDNA to produce a first population of amplification products comprising full length cDNA amplification products, and a second population of amplification products comprising EX3(−) amplification products. In another embodiment, the detecting comprises contacting the cDNA with a probe having full sequence complementarity to both (I) cDNA corresponding to full length opsin gene mRNA; and (II) cDNA corresponding to EX3(−) mRNA, wherein the contacting occurs under conditions suitable for hybridization of the probe to the cDNA.

In various embodiments, the one or more opsin gene is the L-opsin gene, the M-opsin gene, or both.

In another aspect, the invention provides methods for determining a subject's predisposition for refractive error comprising:

(a) testing a biological sample obtained from the subject to identify an opsin gene variant comprising LIVVA (SEQ ID NO: 1), designated as such for the amino acids encoded at positions 153, 171, 174, 178 and 180 of the L or M opsin gene; and (b) correlating the opsin gene variant with a predisposition for refractive error.

In one embodiment, the opsin gene variant comprises LIVVA (SEQ ID NO: 1)/GCGATCGG.

In another embodiment, the methods comprise treating a refractive error in a subject comprising (a) determining a predisposition for refractive error of a subject in accordance with the methods of any embodiment or combination of embodiments of the invention; and (b) treating the subject to slow progression of refractive error.

In another aspect, the invention provides compositions, comprising or consisting of a primer pair capable of selectively amplifying a detectable portion of one or more human opsin genes, wherein the detectable portion includes exon 3.

DETAILED DESCRIPTION OF THE INVENTION

Figure 1:
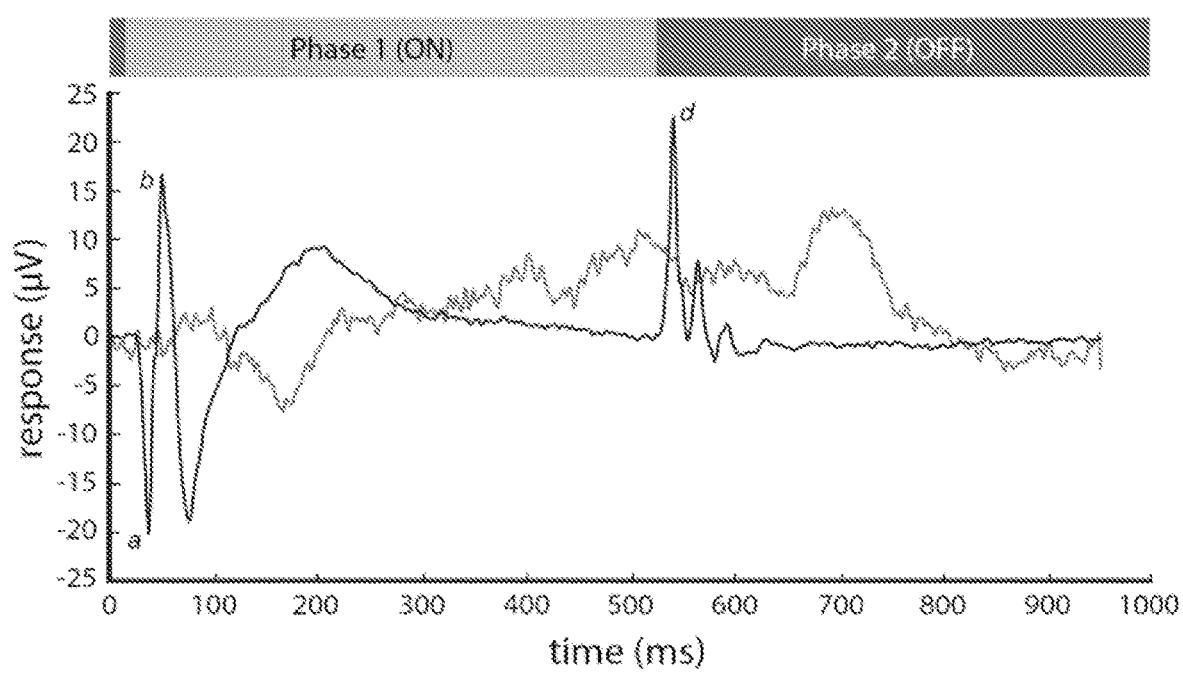
FIG. 1. On-Off L/M cone isolating ERG from the average of subjects with normal opsin variants (n=5) and a subject with the LIAVA (SEQ ID NO: 2) variant as his only X chromosome opsin gene.

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the invention provides methods for determining a subject's predisposition for refractive error comprising:

(a) testing a biological sample obtained from the subject to determine exon 3 splicing defects in one or more opsin gene; and (b) correlating the exon 3 splicing defects in the one or more opsin gene with a predisposition for refractive error.

As shown in the examples that follow, the inventors have developed methods to determine exon 3 splicing defects in L and M cone opsin genes and demonstrated that such exon 3 splicing defects account for an unexpectedly high percentage of refractive error variance in human subjects. Thus, the methods may be used for identifying subjects at risk of developing refractive errors and predicting the potential severity of refractive errors, and providing early treatment for such subjects and to help in decision making about the most effective treatment for individual subjects.

The subject may be any subject, such as a human subject.

As used herein, a "refractive error" is an error in the focusing of light by the eye of the subject, generally due to the shape of the eye (length of the eyeball, change in shape of the cornea, aging of the lens, etc.) The methods may detect predisposition to any refractive error, including but not limited to myopia, hyperopia, presbyopia, astigmatism, and blue cone monochromacy.

In one specific embodiment, the refractive error is myopia (nearsightedness). Myopia is most commonly corrected through the use of corrective lenses, which have a negative optical power that compensates for the excessive positive diopters of the myopic eye. A "diopter" is the unit of measurement of the optical power of a lens, which is equal to the reciprocal of the focal length. Negative diopters are generally used to describe the severity of the myopia, as this is the value of the lens to correct the eye. In one embodiment, the methods are used to determine a predisposition to high-grade myopia, defined as −6 diopters or worse. In another embodiment, the myopia is juvenile onset myopia (i.e., prior to reaching 18 years of age).

In another specific embodiment, the refractive error is blue cone monochromacy, an X-linked retinal disorder that affects only males and leads to significant refractive error.

The term "biological sample" as used herein may include any suitable such sample, including but not limited to, blood, saliva, cells from buccal swabbing, biopsies of skin, amniotic fluid, and various other tissues. In specific embodiments, the biological sample is saliva or blood.

As used herein, an "exon 3 splicing defect" means skipping of the entire exon 3 in the mRNA encoded by the opsin gene. As will be understood by those of skill in the art, such defects may include skipping of some/all of other exons, such as exon 2 and/or 4 of the opsin gene being assesses.

Any suitable means for testing the biological sample for exon 3 splicing defects in the one or more opsin gene (L opsin and/or M opsin genes) may be used in the methods of the invention. The methods may be carried out in the sample, or nucleic acid in the sample may be purified or partially purified. Methods for purifying or partially purifying nucleic acids including opsin genes from the biological sample for use in the methods of the invention are known in the art. The nucleic acid can be, for example, genomic DNA, RNA, or cDNA.

In one embodiment, the testing comprises testing the biological sample obtained from the subject to determine the relative amount full length opsin gene mRNA compared to exon 3-skipped opsin gene mRNA ("EX3(−) mRNA"); and wherein the correlating comprises correlating the relative amount of full length opsin gene mRNA to EX3(−) mRNA with a predisposition for refractive error.

As used herein EX3(−) mRNA means mRNA from the one or more opsin gene that completely lacks regions encoded by exon 3 in the opsin gene. In this embodiment, the relative amounts of full length opsin mRNA are compared to EX3(−) mRNA to determine predisposition for refractive error. Any suitable method for determining the relative amounts of full length vs. EX3(−) mRNA may be used. In one embodiment, determining the relative amount of full length opsin gene mRNA to EX3(−) mRNA comprises:

(i) generating amplification products from cDNA of opsin gene mRNA present in the biological sample, wherein the amplification products span exon 3; and (ii) detecting amplification products corresponding to full length opsin gene mRNA and amplification products corresponding to EX3(−) mRNA.

In this embodiment, opsin gene mRNA is reverse transcribed to produce cDNA, which is further amplified to permit detection of the relative amount of full length opsin gene mRNA to EX3(−) mRNA. Such detection can be carried out by any suitable means. In one exemplary embodiment, detecting the amplification products comprises generating a primer extension product from the amplification products using a primer that binds to the amplification products adjacent to an end of exon 3. In this embodiment, the primer used binds to the cDNA such that when a polymerase extends the primer during the primer extension assay, the nucleotide added indicates whether exon 3 (full length) or exon 4 is spliced to exon 2 ((EX3(−)). As used herein, "adjacent" means at a position whereby primer extension from that position is capable of detecting both full length or EX3(−) opsin mRNA. In various embodiments, the primer binds to the amplification product in exon 2 or exon 4 within 1 or 2 nucleotides of the junction between exon 2 and exon 3, or exon 4 and exon 3, of the opsin gene. The primer used in the primer extension assay may, for example, be complementary to a conserved region of exon 2 or 4, as described in more detail below.

The resulting primer extension product may be detected by any suitable technique. In one embodiment, the primer extension product is detected by mass spectrometry, such as MALDI-TOFF Mass Spectrometry. For example, a single-base extension of a primer that anneals directly adjacent to the first informative position on the amplification product (i.e.: the first nucleotide that distinguishes between the presence or absence of exon 3 in the amplification product). The primer extension product is dependent upon the presence or absence of exon 3 in the template sequence, resulting in a difference in mass between extension products.

By way of non-limiting example, a primer used for primer extension may be on either side of the relevant exon:exon junction (i.e.: exon 2 spliced to exon 4 (exon 3 skipped); exon 2 spliced to exon 3 (no skip); exon 3 spliced to exon 4 (no skip). In the case of exon 2 spliced to exon 4, the sequence below shows the resulting cDNA with the exon:exon junction denoted by ||. In one embodiment the underlined region on either side of the junction may be used for primer extension so long as the primer crosses the exon/exon junction and extends to the one base before the first position after the junction that differs between exon 2 spliced to exon 3 versus exon 2 spliced to exon 4 (denoted in bold and somewhat larger font). The extension step has to incorporate the bold and italicized base (T in the example shown below) when the primer extends from exon 2 toward exon 3/4 or the complement to the bold and larger font base (also T in the example shown below) when the primer extends from exon 4 toward exon 2/3.

(SEQ ID NO: 6)
5'GCCCCTTCGAAGGCCCGAATTACCACATCGCTCCCAGATGGGTGTACC

ACCTCACCAGTGTCTGGATGATCTTTGTGGTCAYTGCATCCGTCTTCACA

AATGGGCTTGTGCTGGCGGCCACCATGAAGTTCAAGAAGCTGCGCCACCC

GCTGAACTGGATCCTGGTGAACCTGGCGGTCGCTGACCTRGCAGAGACCG

TCATCGCCAGCACTATCAGCRTTGTGAACCAGGTM<u>TCTGGCTACTTCGTG</u>

<u>CTGGGCCACCCTATGTGTGTCCTGGAGGGCTACACCGTCTCCCTGTG</u>T

G||TACTGGCCCCACGGCCTGAAGACTTCATGCGGCCCAGACGTGTTC

AGCGGCAGCTCGTACCCCGGGGTGCAGTCTTACATGATTGTCCTCATGGT

CACCTGCTGCATCAYCCCACTCRYSATCATCRTGCTCTGCTACCTCCAAG

TGTGGCTGGCCATCCGAGCG 3'

Thus, in one embodiment the extension primer may correspond to the sequence shown over its full length to at least the 12 contiguous 3' residues (underlined) of the following sequence (SEQ ID NO: 7)

5'TCTGGCTACTTCGTGCTGGGCCACCCTATGTGTGTCCTGGAGGGCTAC

<u>ACCGTCTCCCTGTG</u>TG||G 3'.

In various further embodiments, the primer is complementary over its full length the underlined sequence, or to at least 15, 20, 25, 30, 35, or the complete sequence of SEQ ID NO: 16:

(SEQ ID NO: 16)
5'G||<u>GTACTGGCCCCACGGCCTGAAGACTTCATGCGGCCCAGACGTGTT

CAGCGGCAGCTCGTACCCCGGGGTGCAGTCTTACATGATTGTCCTCATGG

TCACCTGCTGCATCAYCCCACTCRYSATCATCRTGCTCTGCTACCTCCAA

GTGTGGCTGGCCATCCGAGCG</u> 3'.

The double underlined portion of the sequence is the complement to an extension primer from exon 4 going toward exon 3/2.

In these embodiments, the assay is designed so that the polymerase adds one nucleotide and the two possible resulting products are: Exon2 . . . TGTG|GG . . . Exon 3 (i.e.: representing full length opsin mRNA) versus Exon 2 . . . TGTG|GT . . . Exon 4 (representing Ex3(−) opsin mRNA). The primer binds immediately upstream of the bold-font nucleotide and it corresponds in sequence to that shown and thus binds to the complementary strand, and incorporates the bold nucleotide shown, so that the polymerase incorporates the bold-font nucleotide. The assay is directional, and thus there is only one possible way to go from exon 2 toward exon 3/4 and only one possible way to go from exon 4 toward exon 3/2.

In another embodiment primer may be complementary over its full length to at least the 12 contiguous 3' residues (underlined) of the following sequence (SEQ ID NO: 10)

5'G||GTACTGGCCCCACGGCCTGAAGACTTCATGCGGCCCAGACGTGTT

CAGCGGCAGCTCGTACCCCGGGGTGCAGTCTTACATGATTGTCCTCATGG

<u>TCACCTGCTGCATCA</u>. 3'.

In various further embodiments, the primer is over its full length to at least 15, 20, 25, 30, 35, or the complete sequence of SEQ ID NO: 10.

In another embodiment, determining the relative amount of full length opsin gene mRNA to EX3(−) mRNA comprises:

(i) generating cDNA of opsin gene mRNA present in the biological sample; and (ii) detecting cDNA corresponding to full length opsin gene mRNA and cDNA corresponding to EX3(−) mRNA.

In this embodiment, opsin gene mRNA is reverse transcribed to produce cDNA, to permit detection of the relative amount of full length opsin gene mRNA to EX3(−) mRNA. Such detection can be carried out by any suitable means. In one exemplary embodiment, detecting the amplification products comprises (i) contacting the cDNA with one or more primer pairs that spans exon 3 and is capable of selectively amplifying the cDNA, under conditions suitable for amplification of the cDNA, and (ii) amplifying the cDNA to produce a first population of amplification products comprising full length cDNA amplification products, and a second population of amplification products comprising EX3(−) amplification products.

In this embodiment, a primer pair is used that will amplify exon 3 if present in the cDNA; as will be understood by those of skill in the art, the primer pair will be designed to base pair with conserved sequences in the opsin gene. In this embodiment, determining the relative amount of full length opsin gene mRNA compared to EX3(−) mRNA comprises determining a relative amount of the first population and the second population of amplification products.

The primer pair can be used in various assays (PCR, RT-PCR, RTQ-PCR, spPCR, qPCR, and allele-specific PCR, etc.) to amplify portions of the one or more opsin gene. The primer pair would include both a "forward" and a "reverse" primer, one complementary to the sense strand and one complementary to an "antisense" strand, and designed to hybridize to the one or more opsin gene so as to be capable of generating a detectable amplification product spanning exon 3 (if present) from the cDNA when subjected to amplification conditions. In various embodiments, each member of the primer pair is a single stranded DNA oligonucleotide at least 12, 13, 14, 15, 16, 17, 18, 19, 20, 21, 22, 23, 24, 25, 26, 27, 28, 29, 30, or more nucleotides in length that are fully complementary to a conserved region of the one or more opsin genes. In another embodiment, next generation sequencing (RNA-seq) can be used to enumerate all possible isoforms of the opsin gene and estimate their relative abundances to detect exon skipping and the extend exon skipping. In this embodiment, RNA is reverse transcribed to cDNA and cDNA library made, and subjected to next generation sequencing.

The nucleic acid sequence of the exons in the opsin gene are shown below; those exons that are completely conserved in nucleic acid sequence are so noted, while areas of the exon that vary from one gene/variant to another are identified (in IUB code). The L and M genes are nearly identical over a span of about 40 kilobase pairs (kb). Each gene has six exons. In humans, the first and sixth exons are identical among the L and M genes. Exon 5 differs in a stereotyped fashion between these genes and functionally determines whether the encoded pigment is L or M by specifying amino acid differences responsible for the majority of the spectral difference between L and M pigments. Exons 2, 3 and 4 vary among and between the L and M opsin genes because of the recombination mechanism that generates the exchange mutants; the regions that differ are those noted below.

Exon 1: (no variation)
(SEQ ID NO: 11)
5'<u>ATGGCCCAGCAGTGGAGCCTCCAAAGGCTCGCAGGCCGCCATCCGCAG</u>

<u>GACAGCTATGAGGACAGCACCCAGTCCAGCATCTTCACCTACACCAACAG</u>

<u>CAACTCCACCAGAG</u> 3';

Exon 6: (No variation)
(SEQ ID NO: 12)
5'<u>TTTCGAAACTGCATCTTGCAGCTTTTCGGGAAGAAGGTTGACGATGGC</u>

<u>TCTGAACTCTCCAGCGCCTCCAAAACGGAGGTCTCATCTGTGTCCTCGGT</u>

<u>ATCGCCTGCATGA</u> 3';

Exon 3: variable positions in IUB code and in bold font
(SEQ ID NO: 13)
5'<u>GGATCACAGGTCTCTGGTCTCTGGCCATCATTTCCTGGGAGAGR</u>TGGM

TGGTGGTS**TGCAAGCCCTTTGGCAATGTGAGATTTGATGCCAAGCTGGCC

ATCRTKGGCATTGYCTTCTCCTGGRTCTGGKCTGCTGTGTGGACAGCCCC

GCCCATCTTTGGTTGGAGCAG 3';

Exon 2: variable positions given in IUB code and in bold font.
(SEQ ID NO: 14)
5'<u>GCCCCTTCGAAGGCCCGAATTACCACATCGCTCCCAGATGGGTGTACC</u>

<u>ACCTCACCAGTGTCTGGATGATCTTTGTGGTCA</u>YTGCATCCGTCTTCACA

AATGGGCTTGTGCTGGCGGCCACCATGAAGTTCAAGAAGCTGCGCCACCC

GCTGAACTGGATCCTGGTGAACCTGGCGGTCGCTGACCTRGCAGAGACCG

TCATCGCCAGCACTATCAGCRTTGTGAACCAGGTMTCTGGCTACTTCGTG

CTGGGCCACCCTATGTGTGTCCTGGAGGGCTACACCGTCTCCCTGTGTG

3';

Exon 4: variable positions given in IUB code and in bold font
(SEQ ID NO: 15)
5'<u>GTACTGGCCCCACGGCCTGAAGACTTCATGCGGCCCAGACGTGTTCAG</u>

<u>CGGCAGCTCGTACCCCGGGGTGCAGTCTTACATGATTGTCCTCATGGTCA</u>

CCTGCTGCATCAYCCCACTCRYSATCATCRTGCTCTGCTACCTCCAAGTG

TGGCTGGCCATCCGAGCG 3'.

Stretches of nucleic acids that are underlined are conserved and primer pairs that hybridize along their length within the underlined regions (or a complement thereof) can be used in the methods of this embodiment of the invention. Thus in one non-limiting embodiment the primer pair comprises a forward primer and a reverse primer, wherein one of the forward or the reverse primer base pairs along its full length with a conserved region in exon 1 of the opsin gene, and the other base pairs along its full length with a conserved region in exon 6 of the opsin gene. In another embodiment, one of the forward or the reverse primer base pairs along its full length with a conserved region in exon 1 of the opsin gene, and the other base pairs along its full length with a conserved region in exon 4 of the opsin gene. In a further embodiment, one of the forward or the reverse primer base pairs along its full length with a conserved region in exon 2 of the opsin gene, and the other base pairs along its full length with a conserved region in exon 6 of the opsin gene. In a still further embodiment, one of the forward or the reverse primer base pairs along its full length with a conserved region in exon 2 of the opsin gene, and the other base pairs along its full length with a conserved region in exon 4 of the opsin gene.

| IUB Code | |
| --- | --- |
| R | A or G |
| Y | C or T |

-continued

| IUB Code | |
|---|---|
| S | G or C |
| W | A or T |
| K | G or T |
| M | A or C |
| B | C or G or T |
| D | A or G or T |
| H | A or C or T |
| V | A or C or G |
| N | any base |

The relative amounts of the resulting amplification products can be directly compared by any suitable technique, including but not limited to real time qPCR, mass spectrometry, etc.); such techniques are well within the level of skill in the art based on the teachings herein.

In another embodiment, determining the relative amount of full length opsin gene mRNA to EX3(−) mRNA comprises contacting the cDNA with one or more probes having full sequence complementarity to both (I) cDNA corresponding to full length opsin gene mRNA; and (II) cDNA corresponding to EX3(−) mRNA, wherein the contacting occurs under conditions suitable for selective hybridization of the probe to the cDNA. As used herein, "selective hybridization" means that the one or more probes are fully complementary to at least a portion of the opsin gene target so as to form a detectable hybridization complex under hybridization conditions, where the resulting hybridization complex is distinguishable from any hybridization that might occur with other nucleic acids. The specific hybridization conditions used will depend on the length of the oligonucleotide probes employed, their GC content, as well as various other factors as is well known to those of skill in the art. The probes for use in this embodiment of the invention may be any that selectively hybridize to conserved regions of the opsin gene target, particularly in exons 1, 2, 4, and 6; such regions are disclosed above. The relative amounts of the full length opsin gene mRNA to EX3(−) mRNA can be directly compared in this embodiment by any suitable technique, including but not limited to quantitative hybridization techniques; such techniques are well within the level of skill in the art based on the teachings herein.

In all of these embodiments and combinations of embodiments, the methods permit correlating the exon 3 splicing defects in the one or more opsin gene with a predisposition for refractive error. As demonstrated in the examples that follow, the correlation between exon 3 skipping and refractive error is 89%. That is, if individuals with a high amount of exon 3 skipping, (above 80% skipped) almost all their very high refractive error (i.e.: high grade myopia) is due to skipping. The inventors estimate that individuals with such this high amount of exon 3 skipping represent ½ of 1% of the population (1 in 200). Furthermore, L opsin gene variants in which 12-50% of the mRNA lacks exon 3 occur at a much higher frequency in the population and are estimated to occur in 20% of males and 36% of females or 28% of the population as a whole. These variants account for more than 50% of the variance in refractive error for common juvenile onset myopia, and represent a significant increased risk for myopia in the general population.

In one embodiment, the one or more opsin gene is the L opsin gene; in another embodiment the M opsin gene; in further embodiment both the L opsin gene and the M-opsin gene.

In another aspect, the invention provides methods for determining a subject's predisposition for refractive error comprising:

(a) testing a biological sample obtained from the subject to identify an opsin gene variant LIVVA (SEQ ID NO:1) designated as such for the amino acids encoded at positions 153, 171, 174, 178 and 180 of the L or M opsin gene; and (b) correlating the opsin gene variant with a predisposition for refractive error.

The inventors have surprisingly discovered that the recited opsin gene variant is prognostic for a subject having a predisposition for refractive error. The newly discovered LIVVA (SEQ ID NO:1) variant was found to be among the highest exon-3 skipping variant. The methods may detect predisposition to any refractive error, including but not limited to myopia, hyperopia, presbyopia, astigmatism, blue cone monochromacy, and blinding disorders. The biological sample may be any suitable sample as described above. Methods for purifying or partially purifying nucleic acids (if needed) from the biological sample for use in the methods are well known in the art. The nucleic acid can be, for example, genomic DNA, RNA, or cDNA.

In one embodiment, the opsin gene variant comprises

```
                                              (SEQ ID NO: 1)
LIVVA/GCGATCGG where in exon 3 (below) the variable positions in TUB code RMSRKYRK correspond in order to GCGATCGG (LIVVA).

(SEQ ID NO: 17)
5'GGATCACAGGTCTCTGGTCTCTGGCCATCATTTCCTGGGAGAGRTGGM

TGGTGGTSTGCAAGCCCTTTGGCAATGTGAGATTTGATGCCAAGCTGGCC

ATCRTKGGCATTGYCTTCTCCTGGRTCTGGKCTGCTGTGTGGACAGCCCC

GCCCATCTTTGGTTGGAGCAG 3'
```

In another embodiment of each aspect of the invention, the methods comprise determining a predisposition for refractive error of a subject in accordance with the methods of any embodiment or combination of embodiments of the invention and treating the subject to slow progression of refractive error. Any suitable method for treating the subject may be used, including but not limited to prescribing glasses or contact lenses and by refractive surgery. In certain embodiments, the methods comprise providing blur-inducing lenses, for example as described in International Patent Application Publication No. WO 2010/075319. In one embodiment, the device is a pair of spectacles comprising blur-inducing lenses, where the blur is designed to reduce the relative activities between neighboring cone photoreceptors in the retina which has been shown herein to result in signals that stimulate the eye to grow in length abnormally. The blur-inducing lenses can be made to induce blurring, for example, by one or more of: small bumps or depressions in one or both surfaces of the lenses; inclusions within the lenses of a material different from the lens material; incorporation of higher-level aberrations in the lenses; and coatings or films that induce blur by light scatter, diffusion or diffraction applied to one or both surfaces of the lenses.

In another embodiment, the blur-inducing lenses are contact lenses. The blur-inducing contact lenses can be made to induce blurring, for example, by one or more of: inclusions within the lenses of a material different from the lens material; incorporation of higher-level aberrations in the lenses; providing progressive negative corrections in one or both lenses from the center of the lens to the bottom of the lenses; and coatings or films that induce blur by light scatter, diffusion or diffraction applied to one or both surfaces of the lenses.

In another embodiment, the treating comprises the subject wearing a therapeutic optical device that comprises a wavelength-dependent filter capable of preferentially blocking red light emanating from the display screen prior to entry into the subject's eye, thereby limiting introduction of refractive error in the subject's eye.

As used herein, "treating" means one or more of (a) reducing the incidence of introduction of refractive error in a subject's eye; (b) reducing the severity of subsequently developed refractive error in a subject's eye; and/or (c) limiting or preventing development of symptoms characteristic of refractive error in a subject's eye.

In another aspect, the invention provides compositions, comprising or consisting of a primer pair capable of selectively amplifying a detectable portion of one or more human opsin gene, wherein the detectable portion includes exon 3. The primer pair can be used, for example, in the methods of the invention. The primer pair includes both a "forward" and a "reverse" primer, one complementary to the sense strand and one complementary to an "antisense" strand, and designed to hybridize to the one or more opsin gene so as to be capable of generating a detectable amplification product spanning exon 3 (if present) from the cDNA when subjected to amplification conditions. In various embodiments, each member of the primer pair is a single stranded DNA oligonucleotide at least 12, 13, 14, 15, 16, 17, 18, 19, 20, 21, 22, 23, 24, 25, 26, 27, 28, 29, 30, or more nucleotides in length that are fully complementary to a conserved region of the one or more opsin genes. In various further embodiments, the primer is up to 50, 45, 40, 35, or 30 nucleotides in length.

The nucleic acid sequence of the exons in the opsin gene are shown below; those exons that are completely conserved in nucleic acid sequence are so noted, while areas of the exon that vary from one gene/variant to another are identified (in TUB code). Stretches of nucleic acids that are underlined are conserved and primer pairs that hybridize along their length within the underlined regions (or a complement thereof) can be used in the methods of this embodiment of the invention.

```
Exon 1: (no variation)
                                          (SEQ ID NO: 11)
5'ATGGCCCAGCAGTGGAGCCTCCAAAGGCTCGCAGGCCGCCATCCGCAG

GACAGCTATGAGGACAGCACCCAGTCCAGCATCTTCACCTACACCAACAG

CAACTCCACCAGAG 3';

Exon 6: (No variation)
                                          (SEQ ID NO: 12)
5'TTTCGAAACTGCATCTTGCAGCTTTTCGGGAAGAAGGTTGACGATGGC

TCTGAACTCTCCAGCGCCTCCAAAACGGAGGTCTCATCTGTGTCCTCGGT

ATCGCCTGCATGA 3';

Exon 2: variable positions given in IUB code and
in bold font.
                                          (SEQ ID NO: 14)
5'GCCCCTTCGAAGGCCCGAATTACCACATCGCTCCCAGATGGGTGTACC

ACCTCACCAGTGTCTGGATGATCTTTGTGGTCAYTGCATCCGTCTTCACA

AATGGGCTTGTGCTGGCGGCCACCATGAAGTTCAAGAAGCTGCGCCACCC

GCTGAACTGGATCCTGGTGAACCTGGCGGTCGCTGACCTRGCAGAGACCG
```

```
-continued
TCATCGCCAGCACTATCAGCRTTGTGAACCAGGTMTCTGGCTACTTCGTG

CTGGGCCACCCTATGTGTGTCCTGGAGGGCTACACCGTCTCCCTGTGTG;

Exon 4: variable positions given in IUB code and
in bold font/underlined
                                          (SEQ ID NO: 15)
5'GTACTGGCCCCACGGCCTGAAGACTTCATGCGGCCCAGACGTGTTCAG

CGGCAGCTCGTACCCCGGGGTGCAGTCTTACATGATTGTCCTCATGGTCA

CCTGCTGCATCAYCCCACTCRYSATCATCRTGCTCTGCTACCTCCAAGTG

TGGCTGGCCATCCGAGCG 3'.
```

Stretches of nucleic acids that are underlined are conserved and primer pairs that hybridize along their length within the underlined regions (or a complement thereof) can be used in the methods of this embodiment of the invention. Thus in one non-limiting embodiment the primer pair comprises a forward primer and a reverse primer, wherein one of the forward or the reverse primer base pairs along its full length with a conserved region in exon 1 of the opsin gene (i.e.: any stretch of at least 12 contiguous nucleotides in exon 1), and the other base pairs along its full length with a conserved region in exon 6 of the opsin gene (i.e.: any stretch of at least 12 contiguous nucleotides in exon 6). In another embodiment, one of the forward or the reverse primer base pairs along its full length with a conserved region in exon 1 of the opsin gene, and the other base pairs along its full length with a conserved region in exon 4 of the opsin gene (i.e.: any stretch of at least 12 contiguous nucleotides in exon 4 between nucleotides 1-110 or 129-166). In a further embodiment, one of the forward or the reverse primer base pairs along its full length with a conserved region in exon 2 of the opsin gene (i.e.: any stretch of at least 12 contiguous nucleotides in exon 2 between nucleotides 1-81, 83-187, 189-218, 220-232, or 244-307), and the other base pairs along its full length with a conserved region in exon 6 of the opsin gene. In a still further embodiment, one of the forward or the reverse primer base pairs along its full length with a conserved region in exon 2 of the opsin gene, and the other base pairs along its full length with a conserved region in exon 4 of the opsin gene.

In one non-limiting embodiment, the primer pair comprises:

(a) a first primer comprising 12 or more contiguous nucleotides of SEQ ID NO: 14 (exon 2) nucleotides 1-81, 83-187, 189-218, 220-232, or 244-307, or a full complement thereof; and (b) a second primer pair comprising 12 or more contiguous nucleotides of SEQ ID NO: 15 (exon 4) nucleotides 1-110 or 129-166, or a full complement thereof.

In another non-limiting embodiment, the primer pair comprises:

(a) a first primer comprising 12 or more contiguous nucleotides of SEQ ID NO: 11 (exon 1), or a full complement thereof; and (b) a second primer pair comprising 12 or more contiguous nucleotides of SEQ ID NO: 12 (exon 6), or a full complement thereof.

In a further embodiment, the primer pair may be detectably labeled. Any suitable label can be used. In various non-limiting embodiments, useful detectable labels include but are not limited to radioactive labels such as $^{32}P$, $^{3}H$, and $^{14}C$; fluorescent dyes such as fluorescein isothiocyanate (FITC), rhodamine, lanthanide phosphors, and Texas red, ALEXIS® (Abbott Labs), CY® dyes (Amersham); electron-dense reagents such as gold; enzymes such as horseradish peroxidase, beta-galactosidase, luciferase, and alkaline phosphatase; colorimetric labels such as colloidal gold; magnetic labels such as those sold under the mark DYNABEADS®; biotin; dioxigenin; or haptens and proteins for which antisera or monoclonal antibodies are available. The label can be directly incorporated into the primer, or it can be attached to a probe or antibody which hybridizes or binds to the primer. The labels may be coupled to the primer by any suitable means known to those of skill in the art. In various embodiments, the primers are labeled using nick translation, PCR, or random primer extension (see, e.g., Sambrook et al. supra).

EXAMPLES

Introduction

Many human diseases involve gene-splicing errors, including cystic fibrosis, Duchenne muscular dystrophy, and retinitis pigmentosa. Recently, Ueyama et al (Biochem Biophys Res Commun, 424, 152, 2012) found that variants of the cone opsin genes associated with red-green color vision deficiency led to splicing errors that resulted in the absence of exon 3 from the final mRNA. The human L and M opsin genes are highly variable and we designed an assay to survey opsin gene variants to identify those associated with exon 3 splicing defects. In addition, among the variants associated with exon skipping we sought to quantify the fraction of mRNA that contains normal full-length message compared to message in which exon 3 was skipped.

We designed a minigene test in which HEK293 cells were transfected with a plasmid containing the full length opsin sequence with introns removed except for the two flanking exon 3. mRNA was harvested and used to produce cDNA. For the next step we used the MASS ARRAY® instrument to perform single nucleotide level genetic analysis by allele specific primer extension followed by mass spectrometry. The assay was designed to quantify the fraction of L opsin mRNA that lacked exon 3. The assay was first tested and calibrated with known mixtures of full length and exon skipped cDNA. It was then used to probe exon skipping across all 128 variants of L opsin exon 3. We took advantage of the ability of mass spectrometry to quantitate the relative amounts of full length vs. exon 3 skipped opsin mRNA. However this is only one possible implementation of the method; any quantitative method capable of determining the relative amounts of the two mRNA species could be used.

The exon skipping assay was found to be accurate within 5%. Across all exon 3 opsin variants a surprising number were associated with exon 3 splicing defects in which some amount of mRNA lacked exon 3. Across all variants tested the median fraction of mRNA in which exon 3 was skipped was 9% and the mean 25%. LIAVA (SEQ ID NO: 2), LVAVA (SEQ ID NO: 4) and LIVVA (SEQ ID NO: 1) encoding haplotypes were found to be among the highest skipping variants. Sequences encoding an alanine instead of serine at position 180 skipped more on average (38% versus 11%), as did sequences encoding valine instead of isoleucine at position 178 (44% vs 6%).

```
                        (SEQ ID NO: 2)
    LIAVA, (SEQ ID NO: 4)
    LVAVA
    and (SEQ ID NO: 1)
    LIVVA
``` haplotypes, which were among the highest skipping haplotypes, are all associated with extremely high-grade myopia. The association between particular opsin gene haplotypes and refractive errors has been reported previously, but the effect of different variants on the cell biology of the photoreceptors was unknown. Thus, thus there was no way of predicting a priori, which haplotypes would predispose people to acquire refractive errors. Now the discovery that the refractive errors are associated with splicing defects makes it possible to determine if any individual haplotype will predispose a person to having a refractive error by using the assay we have developed to quantitate the relative amounts of full length vs. exon 3 skipped opsin mRNA.

There are current treatments available that slow the progression of refractive errors in children that are susceptible and several additional therapies are under development. In order for the treatments to be the most effective, there is a need to identify children who are susceptible before any refractive errors are manifest. The method we have developed fulfills that need.

Background

The discovery that red-green colorblindness is the result of rearrangement of the cone photopigment genes on the X-chromosome at Xq28 led to extensive research over the last decades into genotype-phenotype correlations between mutations in the X-chromosome opsin gene array and colorblindness (for review see [1]). The long-(L) and middle-(M) wavelength cones make up 95% of our cones, and except at very low light levels when rods are active, all vision is based on cones. Thus, every aspect of seeing, not just seeing color, depends on the L and M cone photopigments. The L and M cone opsin genes, designated OPN1LW and OPN1MW, respectively, are highly variable in the sequences of exon 2, 3 and 4. Because of the essential role of the photopigments in vision and other processes such as visually guided eye growth, genetic variations in these genes are important risk factors for common eye disorders that plague modern humans. We have studied in detail two opsin gene variants, designated LIAVA (SEQ ID NO: 2) and LVAVA (SEQ ID NO: 4) for the amino acids encoded at positions 153, 171, 174, 178 and 180 of the opsins. We discovered that these opsin gene variants are associated with photoreceptor dysfunction and severe vision impairment [2-6]. These variants are found in patients with clinical diagnoses ranging from color blindness, high myopia, cone dystrophy, blue cone monochromacy, Bornholm Eye Disease, and glaucoma. These variants have never been observed in individuals without vision deficits.

With the advent of next generation sequencing technologies, there has been an explosive increase in the number of genome sequence variations identified in disease-associated genes. The primary focus in trying to understand the pathophysiology of these sequence variations has been on non-synonymous variations that alter the protein coding regions or change promoters and well-characterized core splicing signals that affect gene expression. Other sequence variations are often ignored or classified as neutral, yet there are abundant examples in which the pathophysiologic effects of silent or missense mutations have been assumed to be exerted at the level of protein function when the main effect is aberrant splicing [9-11]. Knowing whether a genome variation affects splicing, protein function, or both is critically important if effective treatments are to be developed. Insight into the Unique Mutational Mechanism Generating Variation in OPN1LW and OPN1MW Genes.

Most Old World monkeys and apes have two photopigment genes on the X-chromosome, one L and one M. We assume that ancestors to modern humans had similar X-chromosome gene arrays to those of Old World primates. Rearrangements of the OPN1LW and OPN1MW genes are responsible for red-green colorblindness in humans (for review see [1]) Unequal homologous recombination between opsin genes on two X chromosomes gives rise to new gene arrangements that underlie colorblindness. Relaxation of selection against colorblindness in modern humans has raised the frequency of carriers in the population. In female carriers, unequal homologous recombination between a "colorblind array", and a normal array can produce an array that underlies normal color vision in males but that has an exchange mutant gene. In the modern population, about 15% of females are carriers, giving many opportunities for recombination between normal and colorblind arrays to produce opsin gene arrays with exchange mutant genes. The degree of genetic variability in the OPN1LW and OPN1MW genes is unique to modern humans. Old World monkeys and apes have stereotyped L and M opsin genes and presumably, ancestral humans were similar to Old World primates. Thus, intermixing OPN1LW and OPN1MW genes is a degenerative process that is a unique product of human evolution, resulting from reduced selection against color vision deficiencies.

The OPN1LW and OPN1MW genes are nearly identical over a span of about 40 kilobase pairs (kb). Each gene has six exons. In humans, the first and sixth exons are identical among OPN1LW and OPN1MW genes. Exon 5 differs in a stereotyped fashion between these genes and functionally determines whether the encoded pigment is L or M by specifying amino acid differences responsible for the majority of the spectral difference between L and M pigments [17]. Exons 2, 3 and 4 vary among and between the L and M opsin genes because of the recombination mechanism that generates the exchange mutants. The majority of the OPN1LW and OPN1MW genes in the population of men with normal color vision are "L/M exchange mutants." We refer to these genetic variants as "L/M exchange mutants" to distinguish them from rare, random mutations.

High Frequency.

The LVAVA (SEQ ID NO: 4) variant can serve as an example of the high frequency exchange mutants compared to the more familiar rare, random missense mutations. By screening a sample of unselected females, we obtained a preliminary estimate that this mutant occurs at a rate greater than 1 in every 400 X-chromosomes. Compare this to the most frequently found rhodopsin mutation in North America, Pro23His; which accounts for 12% of the RP US population [26]. RP affects 1 in 5000 people world-wide but has a somewhat higher frequency in the US [27]. Therefore, the most common rhodopsin mutation in the United States occurs at a rate of about 1 per 40,000 or one chromosome-3 per 80,000. The LVAVA (SEQ ID NO: 4) cone opsin mutant with a prevalence of 1 in 400, is about 200 times more common. The frequency of these mutations makes them very important contributors to vision disorders.

One cannot develop an appreciation of the degree of variability in these genes by examining public databases, which have been generated using next generation sequencing methods that give very short reads and thus the sequences of exons 2, 3 and 4 cannot be identified as belonging to OPN1LW or OPN1MW. The exon 2, 3 and 4 data presented in the 1000 genomes project (UCSC Genome Browser website) as being only from OPN1LW must necessarily represent a mixture of sequences from both genes. In addition, the dataset is weirdly skewed by underlying assumptions, for example the assumption that exon 3 from OPN1LW always specifies Serine at position 180, and thus provides no information about the prevalence of LIAVA (SEQ ID NO: 2) or LVAVA (SEQ ID NO: 4). In our sample, 158 subjects (~40%) had an OPN1LW gene specifying Alanine at position 180. Nevertheless, in the 1000 genomes project, the combination LIAVS (SEQ ID NO: 3), which was previously reported to underlie blue cone monochromacy in a male with a single X-chromosome opsin gene [5, 28] is found at a frequency 1 in 1659 X chromosomes, which is more than 40 times more common the Pro23His mutation in ADRP. Collectively, the OPN1LW and OPN1MW exon 3 haplotypes that contribute to vision impairment occur at high frequency. All of the other public databases only report the frequency of individual SNPs, not the combinations, and of course, the combinations are essential for understanding the role in vision pathology.

Coding sequence mutations in the cone opsin genes can exert deleterious effects on photoreceptors and vision through aberrant splicing, aberrant protein structure/function, or both. We examined both splicing and protein function for the LIAVA (SEQ ID NO: 2) and LVAVA (SEQ ID NO: 4) variants. For both variants, we examined humans with vision problems who had a single X-chromosome cone opsin gene using a cone-isolating ON-OFF ERG that we developed [29], and behavioral tests of color vision. We also studied genetically engineered mice that we had created by replacing the endogenous X-chromosome cone opsin gene with a cDNA encoding either an LIAVA (SEQ ID NO: 2), LVAVA (SEQ ID NO: 4), or control LIAIS (SEQ ID NO: 5) variant. The engineered mouse locus was required only to splice out intron 1, the other introns were already removed, thus the mice allowed us to evaluate opsin function in isolation of the splice defect. We also created an S opsin knockout line and crossed the targeted replacement mice with the S opsin knockout so that we could examine the effects of the L opsin without the mouse-specific confounding factor of S opsin expression in the L/M photoreceptors [30]. Finally, we made minigenes from our human subjects with the LIAVA (SEQ ID NO: 2) and LVAVA (SEQ ID NO: 4) variants, and from control normal subjects with the LIAIS (SEQ ID NO: 5) variant. We conducted minigene assays in duplicate using DNA from at least two different subjects per variant in order to evaluate the effects on splicing. We summarize the results of these studies below.

LIAVA (SEQ ID NO: 2).

Figure 2:
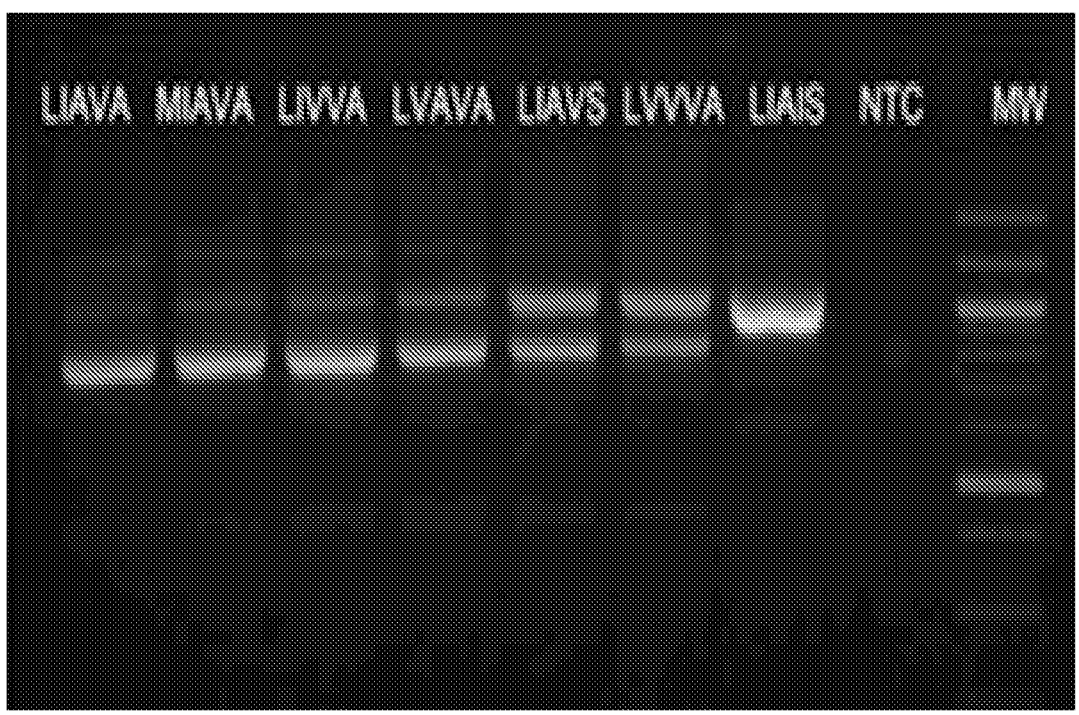
FIG. 2. Minigene assay showing complete exon 3 skipping for two LIAVA (SEQ ID NO: 2) subjects, both exon 3 inclusion and skipping for two LVAVA (SEQ ID NO: 4) subjects, and complete exon 3 inclusion for a control subject.

Humans who we've shown to have an LIAVA (SEQ ID NO: 2) variant of the OPN1LW or OPN1MW gene exhibit a complete absence of function of the corresponding cone, but retain function of their S cones and other L/M cones [2-4]. Adaptive optics imaging of a dichromat who had a normal L opsin and an LIAVA (SEQ ID NO: 2) M opsin suggests that the LIAVA (SEQ ID NO: 2) cones survive and are identifiable as dark spaces in images of the photoreceptor mosaic, but the cones are "invisible" because they do not act as waveguides [4]. Furthermore, this subject's cone mosaic was stable over time in that every cone seen in the original images appeared in images taken 8 years later (Carroll, et al, unpublished data). We conducted L/M- and S-cone isolating ON-OFF ERGs on the blue cone monochromat with the LIAVA (SEQ ID NO: 2) variant as the only expressed X-chromosome opsin gene. The typical ERG waveform was not detected in the L/M cone-isolating ERG (FIG. 1), but the S-cone isolating ERG was normal. We created minigenes using DNA from two subjects who had a LIAVA (SEQ ID NO: 2)/GCGATCGG (SEQ ID NO: 2) variant and two subjects with a control LIAIS (SEQ ID NO: 5)/GCGATCAT variant. The only differences among the minigenes were in the sequence of exon3. Minigenes were transfected into HEK293 cells, mRNA recovered and analyzed with reverse transcriptase PCR. In addition, we developed an assay to quantify the relative amount of PCR product with and without exon 3 using MALDI-TOFF genotyping with the MassArray instrument (assay not described due to space restrictions). As illustrated in FIG. 2, the minigenes gave rise to mRNA that lacked exon 3. In contrast, the control LIAIS (SEQ ID NO: 5) minigenes only gave rise to full length mRNA.

We also evaluated whether the amino acid sequence of the LIAVA (SEQ ID NO: 2) opsin affected cone function in genetically modified mice. Greenwald et al. [30 1971] describe the structure of the modified opsin locus. Until about 16 months of age, the LIAVA mice did not differ in cone function compared to control mice that had the LIAIS (SEQ ID NO: 5) variant (data not shown). The ERG and immunohistochemistry data obtained from the LIAVA (SEQ ID NO: 2) mice suggest there may be a mild deleterious effect of the amino acid sequence of the LIAVA (SEQ ID NO: 2) variant on photoreceptor function and morphology in old mice.

Collectively, these results indicate that the splicing defect exhibited by the LIAVA (SEQ ID NO: 2)/GCGATCGA opsin variant entirely accounts for the human phenotypes. The splicing defect appears to be complete or nearly complete with no detectable full length mRNA observed with the polymerase chain reaction. The pre-mRNA for the LIAVA (SEQ ID NO: 2) variant contains has a translation termination codon within 50 nucleotides of an exon/exon junction and it is has an excessively long 3' untranslated region. These features target aberrantly spliced mRNAs to the nonsense mediated decay pathway, thereby preventing their translation, and thus aberrant protein is unlikely to contribute to the human phenotypes. The deleterious consequences of the LIAVA (SEQ ID NO: 2) variant for vision appear to be cell autonomous because the human ERG data show the S cones to be functional.

LVAVA (SEQ ID NO: 4).

Figure 3:
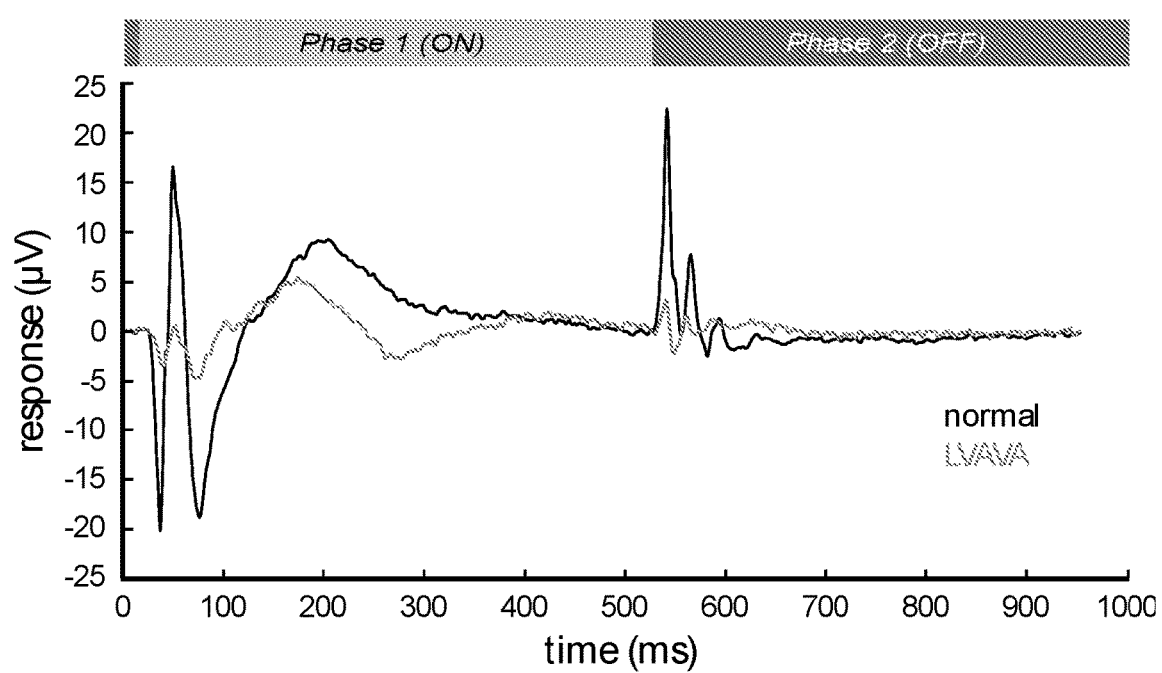
FIG. 3. Averaged L/M-cone isolating ON-OFF ERGs from two subjects with an LVAVA (SEQ ID NO:4) opsin gene as the only X-chromosome opsin gene (n=2, gray trace) compared to the average of subjects with normal opsin genes (n=5, black trace).
Figure 4:
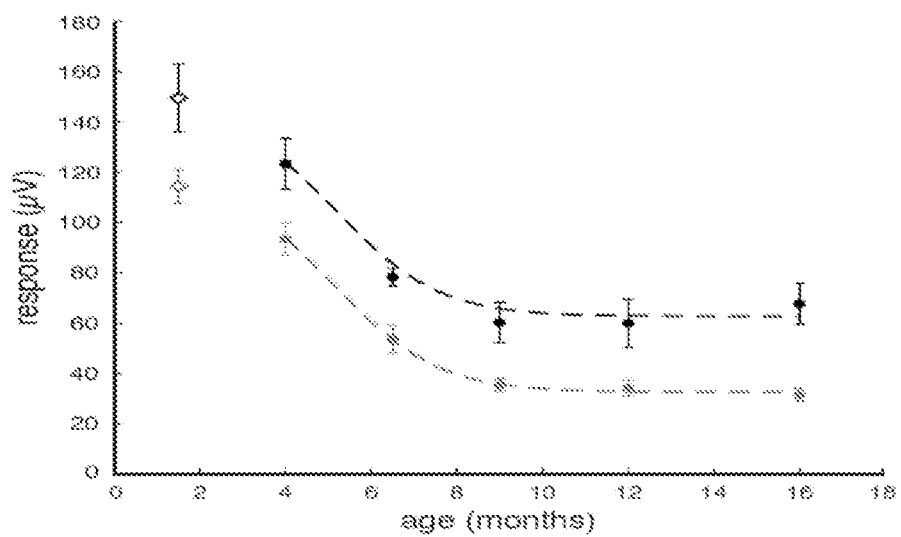
FIG. 4. A. L/M cone isolating On-Off ERG from mice in which a human cDNA for the LIAIS (SEQ ID NO: 5) variant and a human cDNA for the LVAVA (SEQ ID NO: 4) variant replace the endogenous mouse X-chromosome opsin gene. Each data point is the average ERG b-wave amplitude for 10 mice. Except for the mice used for the 1.5 month time point, the data is a longitudinal study of the same group of mice for each variant. B. intensity response functions for the LIAIS (SEQ ID NO: 5) versus LVAVA (SEQ ID NO: 4) mice. The dashed lines show the difference in light intensity required to elicit a response of 6 microvolts for the LIAIS (SEQ ID NO: 5) versus LVAVA (SEQ ID NO: 4) mice, which is a measure of dysfunction of the LVAVA (SEQ ID NO: 4) variant. For both panels, the black symbols are for the LIAIS (SEQ ID NO: 5) mice and the gray symbols are for the LVAVA (SEQ ID NO: 4) mice.
Figure 4:
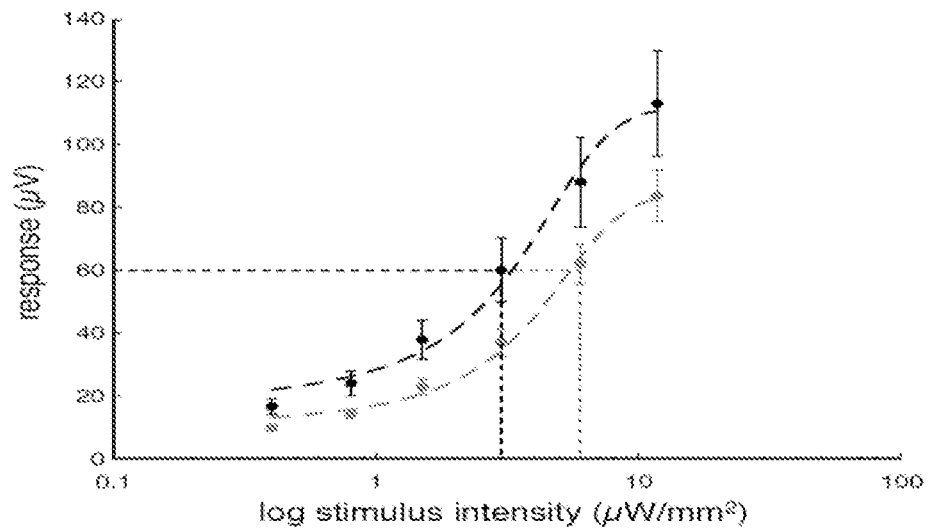

We characterized two males who have an LIAVA (SEQ ID NO: 2)/GCGGGCGG allele as the only X-chromosome cone opsin gene [5]. Both of them self-reported a progressive vision loss from childhood. As young adults, they were diagnosed with cone-rod dystrophy indicating that LVAVA (SEQ ID NO: 4) mutant results in a progressive loss of cone function. The subjects both appeared to be in a late stage of the disease with visual acuities of about 20/200. At this stage, results from imaging with adaptive optics were indistinguishable from BCM phenotypes where mutations, such as locus control region (LCR) deletions, cause an early complete loss of functional L or M cones [5, 31]. Both subjects retained residual L/M cone function (FIG. 3), but there was no measurable S cone function (data not shown). The imaging data suggests that in the central retina where cone density is highest, in addition to degeneration of the LVAVA-opsin (SEQ ID NO: 4) containing cones there is also non-cell autonomous degeneration of the nearby rods and S cones as well [5]. Disruption of the photoreceptor mosaic was much less in locations that are more peripheral. Minigenes made from the LVAVA (SEQ ID NO: 4)/GCGGGCGG opsin genes of these subjects yielded mRNA lacking exon 3, and normal full length mRNA. As for the LIAVA (SEQ ID NO: 2) opsin gene, it is likely that the mRNA lacking exon 3 is targeted to nonsense mediated decay, however the full length mRNA must be translated and is responsible for the residual L/M cone function (FIG. 2). A longitudinal study of the L/M cone isolating ON-OFF ERG in genetically engineered mice showed that at every time point examined (1.5 weeks post-natal, and 3 to 16 months at 3 month intervals), mice with the LVAVA (SEQ ID NO: 4) photopigment had reduced cone function (FIG. 4) compared to the control mice. The engineered locus in the control mice differed from that in the LVAVA (SEQ ID NO: 4) mice only in the sequence of exon 3 (LIAIS (SEQ ID NO: 5)/GCGATCAG). Collectively, these results suggest that the human phenotype associated with the LVAVA (SEQ ID NO: 4) opsin gene allele is due to abnormal protein function, perhaps compounded by a subnormal amount of photopigment in cones because of the splice defect.

Figure 5:
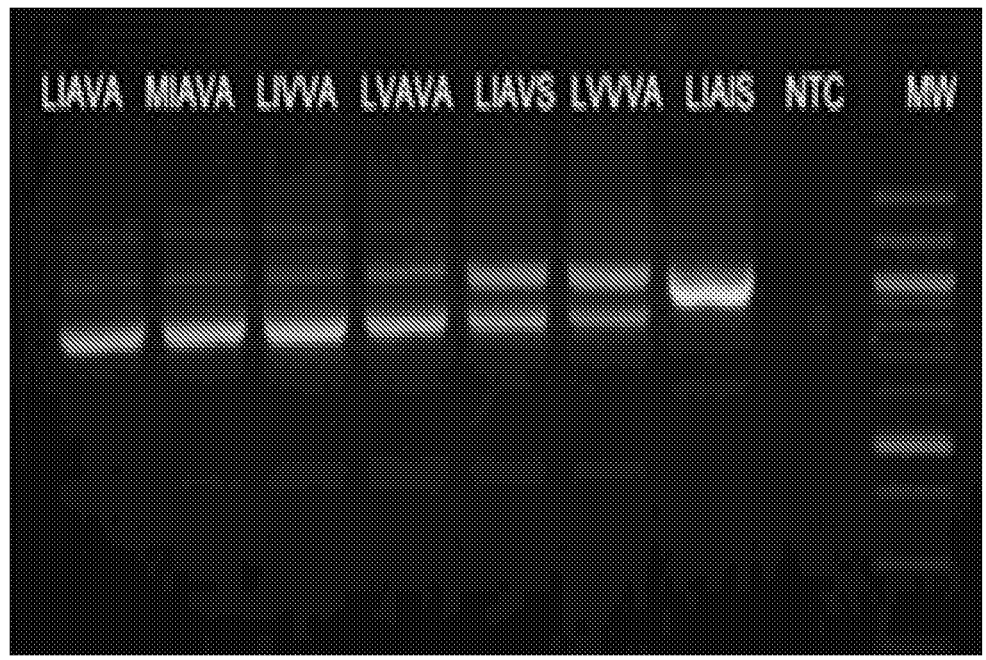
FIG. 5. Minigene assay results showing the gradient of exon 3 skipping for different variants. * bands are heteroduplexes between full length and exon3 skipped mRNA. ** mRNA lacking exon 3. NTC is the no template control in the minigene assay. MW are molecular weight markers.

As mentioned above, we recently identified the variant LIVVA (SEQ ID NO: 1)/GCGATCGG (SEQ ID NO: 2) in blue cone monochromat brother and demonstrated aberrant splicing. We previously reported LVVVA (SEQ ID NO: 9)/GCGGGGGG in a patient with a severely disrupted cone mosaic [5], and recently made a minigene with the subjects DNA and found significant exon 3 skipping. In collaboration with M. Michaelides, we identified MIAVA (SEQ ID NO: 8)/AACATCGG, found in a female diagnosed with blue cone monochromacy who had two OPN1LW genes, one encoded LIAVA (SEQ ID NO: 2) the other encoded MIAVA (SEQ ID NO: 8), and a single OPN1MW variant which was MIAVA (SEQ ID NO: 8) and showed that MIAVA (SEQ ID NO: 8) causes exon 3 skipping; Gardner et al. 2014 independently verified this [7]. Finally, LIAVS (SEQ ID NO: 3)/GCGATCGT was previously found associated with blue cone monochromacy, and was demonstrated to cause exon 3 skipping [5, 8, 28]. FIG. 5 is a picture of a gel showing our minigene assay results for these variants and illustrates that there is a gradient of exon 3 skipping bounded by nearly complete exclusion and complete inclusion of exon 3. The variants that give rise to full length mRNA as well as exon 3-skipped message appear to be associated with the most severe disruption of retinal architecture. It remains to be seen whether this is due to deleterious effects due to protein structure/function alterations in the variants, due to translation of the exon 3-skipped mRNA, abnormally low amount of opsin/photopigment, or some combination of these possibilities.

We sought to establish an assay to quantitatively estimate the relative amount of full length mRNA compared to the exon3-skipped mRNA. The assay we developed is based on the polymerase chain reaction (PCR), followed by primer extension and analysis of the products using MALDI-TOFF Mass Spectrometry. For this we have used the MASSARRAY® instrument. However, quantification can be performed by a number of alternative methods.

General Method

A blood or saliva sample was collected from the subject. Genomic DNA was isolated using a commercially available DNA extraction kit according to the manufacturer's instructions. We amplify the OPN1LW and OPN1MW genes following the detailed procedure described in reference 2 (Neitz et al. 2004). The PCR product was cloned into the mammalian expression vector pCMV5a as described in reference 8, and transfected into HEK293 or other suitable cells, also described in reference 8. mRNA was isolated from the cell cultures 24 to 48 hours after transfection. The mRNA was extracted and reverse transcribed using commercially available kits and following the manufacturer's instructions. The cDNA used in PCR with primers that span the spliced region. The reverse PCR primer is: 5'CATGTAAGACTGCACCCCGG (SEQ ID NO: 20). The extension primer is: 5'AGGCCGTGGGGCCAGTACC (SEQ ID NO: 21). Below are maps of the PCR and extension primers.

Below is (EX3(−)) exon 2 spliced to exon 4. Exon 2 is shown in italics, exon 4 is shown in bold, not italics. The forward PCR primer corresponds to the large font, italicized, sequence in exon 2 (5' AACCAGGTCTCTGGCTACTT 3') (SEQ ID NO:19). The reverse primer corresponds to the reverse complement of the bold, large font sequence in exon 4 (CCGGGGTGCAGTCTTACATG) (SEQ ID NO:22). The extension primer is the reverse complement of the underlined sequence that spans the exon/exon junction, which is labeled (G∥GTACTGGCCCCACGGCCT) (SEQ ID NO:23). When the complement of the first T nucleotide upstream of the exon/exon junction (T is in large font below) is added by the polymerase to the extension primer, it indicates that the mRNA is (EX3(−)).

(SEQ ID NO: 24)
*CGTGACCCTCAGGTGATGCGCCAGGGCCGGCTGCCGTCGGGGACAGGGCT*

*TTCCATAGCCATGGCCCAGCAGTGGAGCCTCCAAAGGCTCGCAGGCCGCC*

*ATCCGCAGGACAGCTATGAGGACAGCACCCAGTCCAGCATCTTCACCTAC*

*ACCAACAGCAACTCCACCAGAGGCCCCTTCGAAGGCCCGAATTACCACAT*

*CGCTCCCAGATGGGTGTACCACCTCACCAGTGTCTGGATGATCTTTGTGG*

*TCACTGCATCCGTCTTCACAAATGGGCTTGTGCTGGCGGCCACCATGAAG*

*TTCAAGAAGCTGCGCCACCCGCTGAACTGGATCCTGGTGAACCTGGCGGT*

*CGCTGACCTAGCAGAGACCGTCATCGCCAGCACTATCAGCATTGTGAACC*

*AGGTCTCTGGCTACTT* CGTGCTGGGCCACCCTATGTGTGTCCTGGAGGG

CTACACCGTCTCCCTGTGTG∥G

TACTGGCCCCACGGCCTGAAGACTTCATGCGGCCCAGACGTGTTCAGCGG

CAGCTCGTACCCGGGGTGCAGTCTTACATGATTGTCCTCATGGTCACCT

GCTGCATCATCCCACTCGCTATCATCATGCTCTGCTACCTCCAAGTGTGG

CTGGCCATCCGAGCGGTGGCAAAGCAGCAGAAAGAGTCTGAATCCACCCA

GAAGGCAGAGAAGGAAGTGACGCGCATGGTGGTGGTGATGATCTTTGCGT

ACTGCGTCTGCTGGGGACCCTACACCTTCTTCGCATGCTTTGCTGCTGCC

AACCCTGGTTACGCCTTCCACCCTTTGATGGCTGCCCTGCCGGCCTACTT

TGCCAAAAGTGCCACTATCTACAACCCCGTTATCTATGTCTTTATGAACC

GGCAGTTTCGAAACTGCATCTTGCAGCTTTTCGGGAAGAAGGTTGACGAT

GGCTCTGAACTCTCCAGCGCCTCCAAAACGGAGGTCTCATCTGTGTCCTC

GGTATCGCCTGCATGAGGTCTGCCTCCTACCCATCCCGCCCACCGGGGCT

TTGGCCACCTCTCCTTTCCCCCTCCTTCTCCATCCCTGTAAAATAAATGT

AATTTATCTTTGCCAAAACCAA.

The PCR product was gel purified, and used in the MASSARRAY® (Agena) primer extension protocol and purified according to the manufacturer's instructions. The primer extension products were spotted on the MASSARRAY® chip, and analyzed on a mass spectrometer. The instrument software reports the area under the curve for each of the products detected. The ratio of the areas under the curves for the resolved PCR products is calculated and taken as an estimate of the ratio of correctly and incorrectly spliced mRNA.

We validated the assay by performing a standard curve using cDNA we created lacking exon 3 and full length cDNA. We mixed these in known ratios, and estimated the ratios using the MASSARRAY® assay. The assay was accurate within 5%.

We created minigenes for OPN1LW for 128 possible combinations of the SNPs in exon 3 and with exon 2 SNPs being c.194C, c.300A, c.331A, c.362C and exon 4 SNPs being c.689C, c.697G, c.698C, c.699T, c.706A. The exon 3 haplotypes were all possible combinations of the nucleotides found in the coding sequence at references positions: c.453, c.457, c.465, c.511, c.512, c.513, c.521, c.532, c.538 (the translational start is designated c.1). The number of replicates used to calculate the average was 2, 3 or 4. We have a database of 1005 people with normal color vision, and 893 of them had haplotypes that we tested in the minigene assay.

Figure 6:
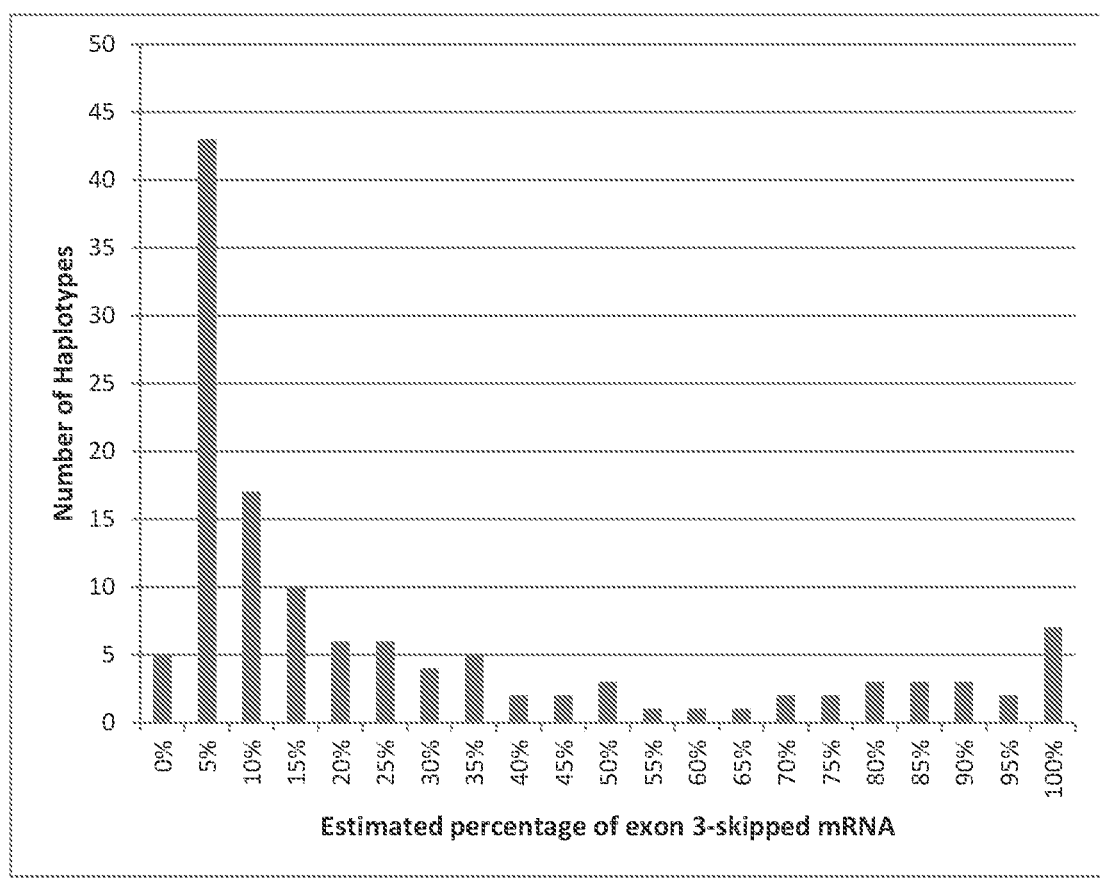
FIG. 6. Histogram of the estimated percentage of exon 3 skipped mRNA for all of the OPN1LW haplotypes investigated.
Figure 7:
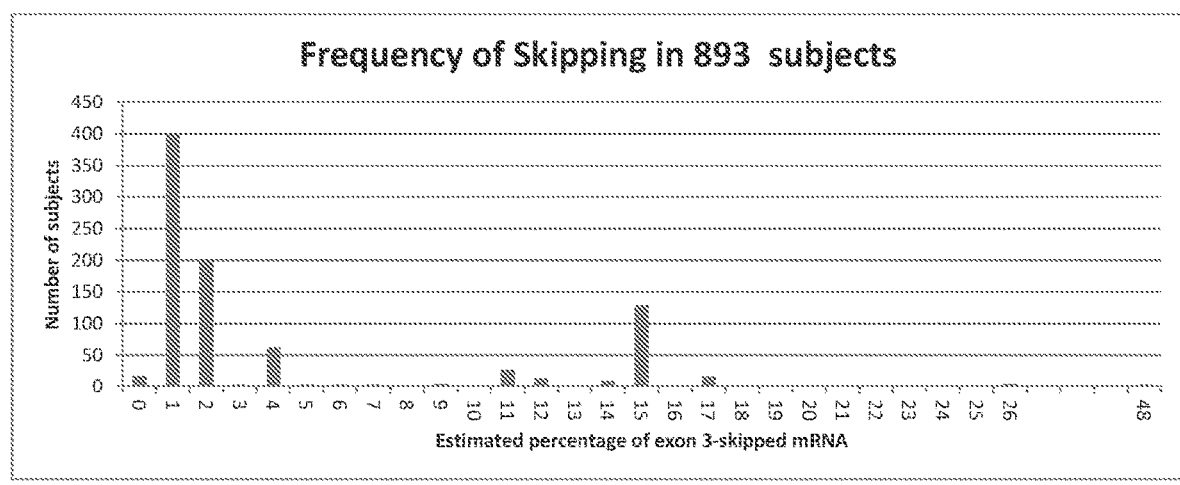
FIG. 7. Histogram showing the estimated percentage of exon 3-skipped mRNA 2 for each of the haplotypes tested 2 that were represented by subjects our pool of subjects with normal color vision. Of the 1005 subjects in our database, 893 of them had a haplotypes that we tested using minigenes and the MASSARRAY® to estimate the proportion of mRNA that lacked exon 3.

FIGS. 6 and 7 summarize the minigene findings. FIG. 6 is a histogram of the data generated showing the average percentage of mRNA with exon 3 skipped (x-axis) versus the number of haplotypes (y-axis). FIG. 6 shows that 43 of the haplotypes tested yielded 5% exon 3-skipped mRNA. Seven of the haplotypes tested only gave rise to exon 3-skipped mRNA, and 5 of the haplotypes did not skip exon 3 at a detectable level. FIG. 7 shows the frequency of exon 3 skipping in 893 people.

Figure 8:
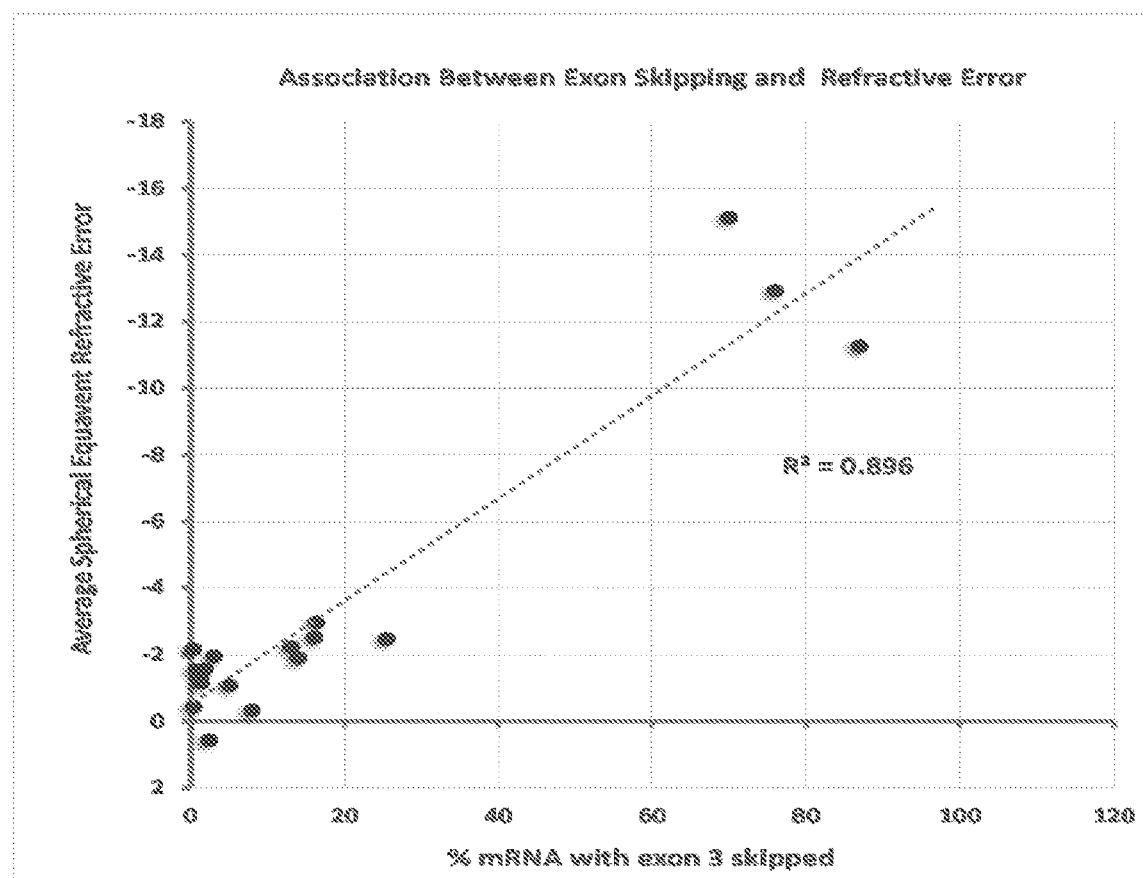
FIG. 8. Association between % L-opsin mRNA with exon 3 skipped as determined by the methods of the invention and amount of refractive error for 18 different commonly occurring L-opsin haplotypes.

In summary, the data in FIGS. 6-8 demonstrate that we have developed an assay to estimate the relative amount of mRNA with exon 3-skipped in a minigene assay. Next we use this data to evaluate the association between haplotypes that show exon 3-skipping and juvenile onset myopia.

Myopia.

Nearsightedness is the most common chronic disorder. It has been a growing problem around the world and in the United States; more than one third of children, although born with normal vision, become nearsighted during their school years. The condition can be corrected by wearing glasses or contact lenses and by refractive surgery, however, because a very large number of people require treatment, these measures are a huge cost to society. The treatments can also have side effects such as infection and surgical complications. The most serious problem, however, is that all currently available solutions correct the refractive errors associated with nearsightedness but do not address the underlying cause. The common forms of myopia are caused by abnormal elongation of the eye during development so that images formed by the lens and cornea are brought to focus in front of the retina. The abnormal eye growth puts people with more severe forms of nearsightedness at risk for retinal detachments, glaucoma, cataract and retinal degeneration.

We have tested the exon 3 skipping assay described above on 18 L-opsin haplotypes determined for adult individuals with known refractive errors. The results indicate that 89% of the variance is attributable to exon skipping. This demonstrates that the exon skipping assay described herein is a highly effective method for determining predisposition to myopia.

In an in vitro minigene assay, minigenes with exon 3 from patients with the LIAVA (SEQ ID NO: 2) variant resulted in mRNA that lacked exon 3. Minigenes with exon 3 from patients with the LVAVA (SEQ ID NO: 4) variant resulted in two alternatively spliced isoforms, normal full length mRNA and mRNA lacking exon 3. Minigenes with exon 3 from normal patients with the control LIAIS (SEQ ID NO: 5) variant resulted only in normal full length mRNA. Our data shows that different combinations of the exon 3 polymorphisms shift the balance between full length and exon 3 skipped mRNA, suggesting that the variants form a gradient of splicing defect that will be extremely useful in elucidating the fundamental mechanisms controlling splicing of this exon.

LITERATURE CITED

1. Neitz, J., and Neitz, M. (2011). The Genetics of Normal and Defective Color Vision. Vision Research 51, 633-651.

2. Neitz, M., Carroll, J., Renner, A., Knau, H., Werner, J. S., and Neitz, J. (2004). Variety of genotypes in males diagnosed as dichromatic on a conventional clinical anomaloscope. Visual Neuroscience 21, 205-216.

3. Crognale, M. A., Fry, M., Highsmith, J., Haegerstrom-Portnoy, G., Neitz, J., Neitz, M., and Webster, M. A. (2004). Characterization of a novel form of X-linked incomplete achromatopsia. Visual Neuroscience 21, 197-204.

4. Carroll, J., Neitz, M., Hofer, H., Neitz, J., and Williams, D. R. (2004). Functional photoreceptor loss revealed with adaptive optics: An alternate cause of color blindness. Proceedings of the National Academy of Sciences of the United States of America 101, 8461-8466.

5. Carroll, J., Dubra, A., Gardner, J. C., Mizrahi-Meissonnier, L., Cooper, R. F., Dubis, A. M., Nordgren, R., Genead, M., Connor, T. B., Jr., Stepien, K. E., et al. (2012). The effect of cone opsin mutations on retinal structure and the integrity of the photoreceptor mosaic. Invest Ophthalmol Vis Sci 53, 8006-8015.

6. McClements, M., Davies, W. I., Michaelides, M., Young, T., Neitz, M., MacLaren, R. E., Moore, A. T., and Hunt, D. M. (2013). Variations in opsin coding sequences cause x-linked cone dysfunction syndrome with myopia and dichromacy. Invest Ophthalmol Vis Sci 54, 1361-1369.

7. Gardner, J. C., Liew, G., Quan, Y. H., Ermetal, B., Ueyama, H., Davidson, A. E., Schwarz, N., Kanuga, N., Chana, R., Maher, E. R., et al. (2014). Three different cone opsin gene array mutational mechanisms with genotype-phenotype correlation and functional investigation of cone opsin variants. Human mutation 35, 1354-1362.

8. Ueyama, H., Muraki-Oda, S., Yamade, S., Tanabe, S., Yamashita, T., Shichida, Y., and Ogita, H. (2012). Unique haplotype in exon 3 of cone opsin mRNA affects splicing of its precursor, leading to congenital color vision defect. Biochem Biophys Res Commun 424, 152-157.

9. Pagani, F., Stuani, C., Tzetis, M., Kanavakis, E., Efthymiadou, A., Doudounakis, S., Casals, T., and Baralle, F. E. (2003). New type of disease causing mutations: the example of the composite exonic regulatory elements of splicing in CFTR exon 12. Hum Mol Genet 12, 1111-1120.

10. Teraoka, S. N., Telatar, M., Becker-Catania, S., Liang, T., Onengut, S., Tolun, A., Chessa, L., Sanal, O., Bernatowska, E., Gatti, R. A., et al. (1999). Splicing defects in the ataxia-telangiectasia gene, ATM: underlying mutations and consequences. Am J Hum Genet 64, 1617-1631.

11. Ars, E., Serra, E., Garcia, J., Kruyer, H., Gaona, A., Lazaro, C., and Estivill, X. (2000). Mutations affecting mRNA splicing are the most common molecular defects in patients with neurofibromatosis type 1. Hum Mol Genet 9, 237-247.

12. Pagani, F., and Baralle, F. E. (2004). Genomic variants in exons and introns: identifying the splicing spoilers. Nat Rev Genet 5, 389-396.

13. Ward, A. J., and Cooper, T. A. (2010). The pathobiology of splicing. The Journal of pathology 220, 152-163.

14. Cooper, T. A., Wan, L., and Dreyfuss, G. (2009). RNA and disease. Cell 136, 777-793.

15. Blencowe, B. J. (2000). Exonic splicing enhancers: mechanism of action, diversity and role in human genetic diseases. Trends Biochem Sci 25, 106-110.

16. Zhang, C., Li, W. H., Krainer, A. R., and Zhang, M. Q. (2008). RNA landscape of evolution for optimal exon and intron discrimination. Proc Natl Acad Sci USA 105, 5797-5802.

17. Neitz, M., Neitz, J., and Jacobs, G. H. (1991). Spectral tuning of pigments underlying red-green color vision. Science 252, 971-974.

18. McClements, M., Neitz, M., Moore, A., and Hunt, D. M. (2010). Bornholm Eye Disease Arises From a Specific Combination of Amino Acid Changes Encoded by Exon 3 of the L/M Cone Opsin Gene. Invest Ophthalmol Vis Sci, ARVO E-Abstract 2609.

19. McClements, M., Davies, W. I., Michaelides, M., Young, T., Neitz, M., Maclaren, R. E., Moore, A. T., and Hunt, D. M. (2013). Variations in opsin coding sequences cause X-linked cone dysfunction syndrome with myopia and dichromacy. Invest Ophthalmol Vis Sci.

20. Cartegni, L., Wang, J., Zhu, Z., Zhang, M. Q., and Krainer, A. R. (2003). ESEfinder: A web resource to identify exonic splicing enhancers. Nucleic Acids Res 31, 3568-3571.

21. Desmet, F. O., Hamroun, D., Lalande, M., Collod-Beroud, G., Claustres, M., and Beroud, C. (2009). Human Splicing Finder: an online bioinformatics tool to predict splicing signals. Nucleic Acids Res 37, e67.

22. Fairbrother, W. G., Yeh, R. F., Sharp, P. A., and Burge, C. B. (2002). Predictive identification of exonic splicing enhancers in human genes. Science 297, 1007-1013.

23. Sironi, M., Menozzi, G., Riva, L., Cagliani, R., Comi, G. P., Bresolin, N., Giorda, R., and Pozzoli, U. (2004). Silencer elements as possible inhibitors of pseudoexon splicing. Nucleic Acids Res 32, 1783-1791.

24. Wang, Z., Rolish, M. E., Yeo, G., Tung, V., Mawson, M., and Burge, C. B. (2004). Systematic identification and analysis of exonic splicing silencers. Cell 119, 831-845.

25. Zhang, X. H., and Chasin, L. A. (2004). Computational definition of sequence motifs governing constitutive exon splicing. Genes & development 18, 1241-1250.

26. Oh, K. T., Longmuir, R., Oh, D. M., Stone, E. M., Kopp, K., Brown, J., Fishman, G. A., Sonkin, P., Gehrs, K. M., and Weleber, R. G. (2003). Comparison of the clinical expression of retinitis pigmentosa associated with rhodopsin mutations at codon 347 and codon 23. American Journal of Ophthalmology 136, 306-313.

27. Weleber, R. G., and Gregory-Evans, K. (2001). Retinitis pigmentosa and allied disorders, (St. Louis: Mosby).

28. Mizrahi-Meissonnier, L., Merin, S., Banin, E., and Sharon, D. (2010). Variable retinal phenotypes caused by mutations in the X-linked photopigment gene array. Investigative Ophthalmology and Visual Science 51, 3884-3892.

29. Kuchenbecker, J. A., Greenwald, S., Neitz, M., and Neitz, J. (2014). Cone-isolating ON-OFF electroretinogram for studying chromatic pathways in the retina. Journal of the optical Society of America A 31, A208-A213.

30. Greenwald, S., Kuchenbecker, J. A., Roberson, R. K., Neitz, M., and Neitz, J. (2014). S-opsin knockout mice with the endogenous M-opsin gene replaced by an L-opsin variant. Visual Neuroscience 31, 25-37.

31. Carroll, J., Rossi, E., Porter, J., Neitz, J., Roorda, A., Williams, D., and Neitz, M. (2010). Deletion of the X-linked opsin gene array locus control region (LCR) results in disruption of the cone mosaic. Vision Research 50, 1989-1999.

We claim:

1. A method for determining a subject's predisposition for refractive error comprising:

(a) testing a biological sample obtained from the subject to determine the relative amount of full length opsin gene mRNA compared to exon 3-skipped opsin gene mRNA ("EX3(−) mRNA");

(b) determining that the subject has a predisposition for refractive error when at least 12% of the opsin gene mRNA is EX3(−) mRNA; and (c) treating the subject to slow progression of refractive error, wherein said treating step comprises the subject wearing blur-inducing lenses.

2. The method of claim 1, wherein determining the relative amount of full length opsin gene mRNA to EX3(−) mRNA comprises:

(i) generating amplification products from cDNA of opsin gene mRNA present in the biological sample, wherein the amplification products span exon 3; and (ii) detecting amplification products corresponding to full length opsin gene mRNA and amplification products corresponding to EX3(−) mRNA.

3. The method of claim 2, wherein detecting the amplification products comprises generating a primer extension product from the amplification products using a primer that binds to the amplification products adjacent to an end of exon 3.

4. The method of claim 3, wherein the primer extension product is detected by MALDI-TOFF Mass Spectrometry.

5. The method of claim 1, wherein determining the relative amount of full length opsin gene mRNA to EX3(−) mRNA comprises:
  (i) generating cDNA of opsin gene mRNA present in the biological sample; and
  (ii) detecting cDNA corresponding to full length opsin gene mRNA and cDNA corresponding to EX3(−) mRNA.

6. The method of claim 5, wherein the detecting comprises
  (i) contacting the cDNA with a primer pair that spans exon 3 and is capable of selectively amplifying the one or more opsin gene, under conditions suitable for amplification of the cDNA, and
  (ii) amplifying the cDNA to produce a first population of amplification products comprising full length cDNA amplification products, and a second population of amplification products comprising EX3(−) amplification products.

7. The method of claim 5, wherein the detecting comprises contacting the cDNA with a probe having full sequence complementarity to both (I) cDNA corresponding to full length opsin gene mRNA; and (II) cDNA corresponding to EX3(−) mRNA, wherein the contacting occurs under conditions suitable for hybridization of the probe to the cDNA.

8. The method of claim 1, wherein the one or more opsin gene comprises an L-opsin gene.

9. The method of claim 1 wherein the one or more opsin gene comprises an M-opsin gene.

10. The method of claim 1, wherein the refractive error is blue cone monochromacy.

11. The method of claim 1, wherein the refractive error is myopia.

12. The method of claim 1, wherein the refractive error is high-grade myopia.

13. The method of claim 1, wherein the refractive error is juvenile onset myopia.

* * * * *